US012590944B2

(12) United States Patent
Nakakubo et al.

(10) Patent No.: US 12,590,944 B2
(45) Date of Patent: Mar. 31, 2026

(54) METHOD AND APPARATUS FOR DETERMINING KETOSIS

(71) Applicant: NATIONAL INSTITUTE FOR MATERIALS SCIENCE, Ibaraki (JP)

(72) Inventors: Ryoh Nakakubo, Ibaraki (JP); Mitsuyoshi Ishida, Ibaraki (JP); Genki Yoshikawa, Ibaraki (JP); Kosuke Minami, Ibaraki (JP); Gaku Imamura, Ibaraki (JP); Hideki Matsuzaka, Ibaraki (JP); Takahiro Nemoto, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 374 days.

(21) Appl. No.: 18/015,792

(22) PCT Filed: Jul. 12, 2021

(86) PCT No.: PCT/JP2021/026065
§ 371 (c)(1),
(2) Date: Jan. 12, 2023

(87) PCT Pub. No.: WO2022/014512
PCT Pub. Date: Jan. 20, 2022

(65) Prior Publication Data
US 2023/0273183 A1 Aug. 31, 2023

(30) Foreign Application Priority Data
Jul. 17, 2020 (JP) ................................. 2020-122610

(51) Int. Cl.
*G01N 33/487* (2006.01)

(52) U.S. Cl.
CPC ................................. *G01N 33/487* (2013.01)

(58) Field of Classification Search
CPC ..................................................... G01N 33/487
(Continued)

(56) References Cited

U.S. PATENT DOCUMENTS

2010/0154714 A1 6/2010 Villiers et al.
2010/0252732 A1* 10/2010 Venditti ................. A61B 5/083
250/289

(Continued)

FOREIGN PATENT DOCUMENTS

JP 5535636 7/2014
JP 2017-167036 9/2017
(Continued)

OTHER PUBLICATIONS

International Search Report (ISR) issued Sep. 28, 2021 in International (PCT) Application No. PCT/JP2021/026065.
(Continued)

*Primary Examiner* — Peter J Macchiarolo
*Assistant Examiner* — Rodney T Frank
(74) *Attorney, Agent, or Firm* — Wenderoth, Lind & Ponack, L.L.P.

(57) ABSTRACT

An object of the present invention is to make it possible to easily determine a presence or absence of ketosis and/or the possibility of ketosis in an animal on site or the like. Another object of the present invention is to provide an apparatus for performing the determination. A method for determining ketosis according to one embodiment of the present invention includes providing gas detection means with a gas generated from a body fluid collected from an animal (except for humans), and determining ketosis of the animal based on a composition of the gas generated from the body fluid using a response of the gas detection means to the gas generated from the body fluid.

16 Claims, 26 Drawing Sheets

(58) Field of Classification Search

USPC ........................................................ 73/31.05

See application file for complete search history.

(56) References Cited

U.S. PATENT DOCUMENTS

| | | | |
|---|---|---|---|
| 2013/0133433 A1 | 5/2013 | Yoshikawa et al. | |
| 2020/0075134 A1* | 3/2020 | Shiba ..................... | G16C 20/70 |
| 2021/0396699 A1 | 12/2021 | Minami et al. | |

FOREIGN PATENT DOCUMENTS

| | | |
|---|---|---|
| WO | 2011/148774 | 12/2011 |
| WO | 2020/110720 | 6/2020 |

OTHER PUBLICATIONS

Shin Oikawa, "Recent Research Trend on Subclinical Ketosis in Dairy Cattle", Journal of the Japan Animal Society, 68, pp. 33-42, 2015, together with machine translation thereof.

A.H. Gustafsson et al., "Milk acetone concentration as an indicator of hyperketonaemia in dairy cows: the critical value revised", Animal Science, 63, pp. 183-188, 1996.

F. Enjalbert et al., "Ketone Bodies in Milk and Blood of Dairy Cows: Relationship between Concentrations and Utilization for Detection of Subclinical Ketosis", Journal of Dairy Science, vol. 84, No. 3, pp. 583-589, 2001.

Extended European Search Report issued Jun. 6, 2024 in corresponding European Patent Application No. 21841598.2.

C. Heuer et al., "Determination of Acetone in Cow Milk by Fourier Transform Infrared Spectroscopy for the Detection of Subclinical Ketosis", Journal of Dairy Science, vol. 84, No. 3, Mar. 1, 2001, pp. 575-582.

Hiroshi Sato, "Increased blood concentration of isopropanol in ketotic dairy cows and isopropanol production from acetone in the rumen", Animal Science Journal, vol. 80, No. 4, May 5, 2009, pp. 381-386.

Communication issued Feb. 20, 2025 in corresponding European Patent Application No. 21841598.2.

* cited by examiner

METHOD AND APPARATUS FOR DETERMINING KETOSIS

TECHNICAL FIELD

The present invention relates to determination of ketosis in animals, and specifically relates to determination of ketosis based on a composition of a gas generated from milk obtained by lactation of an animal as well as a body fluid collected from an animal.

BACKGROUND ART

Ketosis is a state in which production of ketone bodies is mainly enhanced, and a large amount of ketone bodies are accumulated in animal tissues and body fluids due to exceeding utility capacity thereof. For example, a state in which the amount of ketone bodies in blood is increased is also referred to as ketonemia, a state in which the amount of ketone bodies in urine is increased is also referred to as ketonuria, and a state in which the amount of ketone bodies in milk is increased is also referred to as ketolactia. Ketone body is an intermediate metabolite in synthesis and decomposition of fat, and is a generic term for compounds in which a carbonyl group ($>C=O$) and two hydrocarbons ($R-$) are bonded, and examples of the ketone bodies present in an animal body include acetoacetic acid, $\beta$-hydroxybutyric acid (also called 3-hydroxybutyric acid), and acetone.

Fatty acids are decomposed in a liver via acetoacetic acid into acetone or $\beta$-hydroxybutyric acid, and are ultimately oxidized in tissues and metabolized into carbon dioxide and water. When carbohydrate metabolism is impaired, fat stored as an energy source in a living body is used instead of blood glucose, and production of ketone bodies associated with lipolysis is enhanced in the liver. Therefore, when the ketone bodies gradually accumulate in the blood beyond a limit of tissue throughput during impaired glucose utilization due to diabetes, fasting/starvation state, or the like, the ketosis (the ketonemia) occurs.

When the ketosis occurs, gastrointestinal symptoms such as a nausea, a vomiting, and an abdominal pain appear. Since the ketone bodies are acidic substances, the amount of ketone bodies further increases, and when the blood is inclined to be acidic, the ketosis progresses to ketoacidosis (an acidosis state). It is known that when such ketoacidosis continues, a consciousness disorder or a coma state (for example, a diabetic coma) may occur, and in the worst case, death may be caused. Therefore, the ketosis (or the ketoacidosis) is developed by hyperemesis gravidarum, vomiting, diarrhea, dehydration, hyperlipidemia, thyrotoxicosis, digestive absorption disorder, childhood autologous poisoning, glycogen storage disease, and the like, including when utilization of glucose in tissues is impaired (diabetes and the like) and when carbohydrate supply is insufficient (the fasting/starvation state and the like).

Furthermore, it is known that since ruminants produce $\beta$-hydroxybutyric acid from butyric acid, which is a digestive tract fermentation product, a blood ketone body concentration is higher than that of non-ruminants even in a physiological state, and an onset of ketosis is also high. In particular, in dairy cows, a large energy change occurs before and after calving, and a large amount of energy is required with a start of lactation after calving, but an energy balance becomes negative (NEB) in a period in which a dry matter intake (DMI) is not sufficiently increased. Dairy cows try to adapt to this NEB using carbohydrates, proteins, and lipids stored in the body, but in a case where this is not achieved sufficiently, they suffer from the ketosis. While dairy cows suffering from the ketosis show clinical symptoms such as a decrease in DMI and a decrease in milk yield, subclinical ketosis, which is not accompanied by obvious clinical symptoms and in which the ketone bodies in the body are increased, also tends to increase, and there is a problem that this affects the milk yield and the onset of other metabolic diseases.

Conventionally, the concentration of $\beta$-hydroxybutyric acid (BHBA) in blood has been used for the determination of subclinical ketosis in dairy cows (see Non Patent Literature 1). This is because $\beta$-hydroxybutyric acid is more stable than acetone and acetoacetic acid that are other ketone bodies, and as a specific reference value, a range of 1.0 mmol/L to 1.4 mmol/L is shown based on a relationship between the subclinical ketosis, and a subsequent onset of diseases and decrease in productivity. Furthermore, in addition to blood, determination of subclinical ketosis using milk or urine has been performed, and a semi-quantitative method using a test paper has been developed so far. Regarding a diagnosis of subclinical ketosis of dairy cows and the like, Non Patent Literature 1 should be referred as needed.

CITATION LIST

Patent Literature

Patent Literature 1: WO 2011/148774 A
Patent Literature 2: JP 5535636 B2

Non Patent Literature

Non Patent Literature 1: Shin Oikawa, "Recent Research Trend on Subclinical Ketosis", Journal of the Japan Veterinary Medical Association, 68 33-42(2015). (http://nichiju.lin.gr.jp/mag/06801/b1.pdf)
Non Patent Literature 2: A. H. Gustafsson and U. Emanuelson, "Milk acetone concentration as an indicator of hyperketonaemia in dairy cows: The critical value revised", Animal Science 1996, 63: 183-188.
Non Patent Literature 3: F. Enjalbert, M. C. Nicot, C. Bayourthe, and R. Moncoulon, "Ketone Bodies in Milk and Blood of Dairy Cows: Relationship between Concentrations and Utilization for Detection of Subclinical Ketosis", Journal of Dairy Science Vol. 84, No. 3, 2001.

SUMMARY OF INVENTION

Technical Problem

With a recent increase in scales of farms, while a feeding management system of livestock (industrial animals) including dairy cows is changing from individual management to group management, there is a need for early detection of ketosis and subclinical ketosis, which are perinatal diseases.

Although the diagnosis using blood as described above is objective and excellent in accuracy, there are problems that costs tend to be high for a low throughput, and it is difficult to perform a measurement at a breeding site. Recently, a small-sized apparatus capable of on-site measurement has been developed, but since the concentration of $\beta$-hydroxybutyric acid in blood increases after collection, a timing of sampling is limited in order to ensure test accuracy.

The test using urine is noninvasive, but the semi-quantitative method using the test paper that has reached a practical level at present is inferior in accuracy to a blood test. Furthermore, in some animals, it may be difficult to collect a urine specimen, or it may be difficult to use the urine specimen as a sample for diagnosis because there is a restriction on the timing at which the urine specimen can be collected.

Even in the test using milk, usefulness of the semi-quantitative method using the test paper has been confirmed, but there is room for improvement in sensitivity and specificity as compared with the blood test. Moreover, Patent Literature 2 proposes a system that automates ketosis diagnosis and the like from feeding, breast expression, and milk of dairy cows or the like. However, here, since the system is configured based on a technical idea of analyzing a liquid milk as it is, there are problems such as complication of a flow path for inspection and the like (an addition of a reagent flow path for inspection and the like), an increase in consumables cost of a reagent for inspection and the like.

Therefore, an object of the present invention is to enable a presence or absence of ketosis and/or the possibility of ketosis in the animal to be easily determined on site or the like.

Another object of the present invention is to provide an apparatus for performing the determination.

Solution to Problem

In order to solve the above problems, the present inventors have focused on a point that the kind of specimen, that is, the specimen used in a conventional inspection method is all liquid.

For example, in dairy cows, it is disclosed in Non Patent Literature 3 that an acetone concentration in milk is about the same as the acetone concentration in blood and there is a high correlation, but on the other hand, it is known that a smell and taste of milk are different so that it can be clearly distinguished by human sense of smell and taste depending on the difference in the feeding to be fed. In other words, the smell and taste of milk that can be identified by human sense of smell and taste are greatly affected by differences in the feeding. This suggests that even in the milk belonging to one category of cows from a healthy cow, the composition of volatile and evaporative components varies greatly, and thus it may be difficult to distinguish between the volatile and evaporative components of the milk from a cow having a disease when comparing the volatile and evaporative components with each other. Conventionally, in addition to a fact that a practical olfactory sensor was hardly available, it is considered that such possibility was also a cause. However, until now, as far as the present inventors know, almost no knowledge has been obtained on relationship between the gas generated from the milk and the disease.

However, as shown in the examples to be described later, in the measurement using the surface stress sensor as gas detection means, in a case of using a specific sensitive film material, for two kinds of milk obtained from healthy dairy cows having different feeding, a remarkable difference due to the composition of the gas generated from these milk was not confirmed.

From this, the present inventors have conceived, under a hypothesis that a certain correlation can be established between the gas generated from the milk and the disease, without being bound by conventional common knowledge, to perform determination of a specific disease using the gas generated from the milk and a response of the gas detection means to the gas. Furthermore, the present inventors have conceived of an idea that this type of disease determination can be performed for body fluids other than the milk collected from the animal, for example, blood, urine, saliva, and sweat, by using the gas generated therefrom.

As a result of intensive studies, the present inventors have found that it is possible to determine the ketosis of an animal based on the composition of the gas generated from the body fluids such as milk of the animal, and have completed the present invention.

The present invention includes the following summary [1] to [22].

[1] A method for determining ketosis, including: providing gas detection means with a gas generated from a body fluid collected from an animal (except for humans), and determining ketosis of the animal based on a composition of the gas generated from the body fluid using a response of the gas detection means to the gas generated from the body fluid.

[2] The method for determining ketosis according to [1], wherein the body fluid is selected from the group consisting of milk, blood, urine, saliva, and sweat.

[3] The method for determining ketosis according to [1] or [2], wherein the gas generated from the body fluid is at least one of ketones, alcohols, aldehydes, nitriles, organic acids, water (water vapor), nitrogen, oxygen, and carbon dioxide.

[4] The method for determining ketosis according to [3], wherein the gas generated from the body fluid is at least one of ketones and alcohols, the ketones being acetone, and the alcohols being at least one selected from the group consisting of methanol, ethanol, propanol, and butanol.

[5] The method for determining ketosis according to any one of [1] to [4], wherein the gas detection means is a gas sensor, and the response of the gas detection means is a signal output from the gas sensor.

[6] The method for determining ketosis according to [5], in which the determination of ketosis is performed based on a pattern of a temporal change in the signal.

[7] The method for determining ketosis according to [5] or [6], wherein the gas sensor is a surface stress sensor.

[8] The method for determining ketosis according to [7], wherein, as the gas generated from the body fluid, a gas obtained by passing a gas substantially not containing a component that affects the determination of ketosis through a container containing the body fluid is supplied to the surface stress sensor.

[9] The method for determining ketosis according to [7] or [8], wherein the determination of ketosis is performed using the signal after supply of the gas generated from the body fluid to the surface stress sensor is started.

[10] The method for determining ketosis according to any one of [7] to [9], wherein the surface stress sensor is a membrane type surface stress sensor.

[11] The method for determining ketosis according to any one of [7] to [10], wherein at least one selected from the group consisting of poly(4-methylstyrene), poly(2,6-diphenyl-p-phenylene oxide), poly(vinylidene fluoride), cellulose acetate butyrate, poly(ethyleneimine), phenyl group-modified silica/titania composite nanoparticles, and polystyrene is used as a material of a sensitive film of the surface stress sensor.

[12] The method for determining ketosis according to [11], wherein, as the surface stress sensor, at least a first surface stress sensor using one material selected from the group as the sensitive film and a second surface stress sensor using another material selected from the group as the sensitive film are used.

[13] The method for determining ketosis according to any one of [7] to [12], wherein the gas generated from the body fluid and a purge gas are alternately supplied to the surface stress sensor, and the determination of ketosis is performed using the signal corresponding to the gas generated from the body fluid and the signal corresponding to the purge gas.

[14] The method for determining ketosis according to [13], wherein a time frame during which a predetermined reference gas is given to the surface stress sensor is provided in addition to a time frame during which the gas generated from the body fluid is supplied to the surface stress sensor and a time frame during which the purge gas is given to the surface stress sensor, and the signal corresponding to the reference gas is further used in the determination of ketosis.

[15] The method for determining ketosis according to [13], wherein a reference gas and the purge gas are alternately supplied to the surface stress sensor to prepare digital data corresponding to the reference gas, the digital data corresponding to the reference gas being based on the signal corresponding to the reference gas and the signal corresponding to the purge gas, the gas generated from the body fluid and the purge gas are alternately supplied to the surface stress sensor to prepare digital data corresponding to the body fluid to be measured, the digital data corresponding to the body fluid to be measured being based on the signal corresponding to the gas generated from the body fluid and the signal corresponding to the purge gas, and the determination of ketosis is performed based on the digital data corresponding to the reference gas and the digital data corresponding to the body fluid to be measured.

[16] The method for determining ketosis according to [15], wherein the surface stress sensor to which the reference gas and the purge gas are alternately supplied and the surface stress sensor to which the gas generated from the body fluid and the purge gas are alternately supplied are the same surface stress sensor, or are surface stress sensors that are different from each other.

[17] The method for determining ketosis according to any one of [14] to [16], wherein the reference gas is a gas generated from a reference body fluid.

[18] The method for determining ketosis according to any one of [7] to [17], wherein the gas generated from the body fluid is supplied to an additional gas sensor, and the determination of ketosis is performed based on the signal from the surface stress sensor and the signal from the additional gas sensor.

[19] An apparatus for determining ketosis including: at least one surface stress sensor, a first gas flow path for supplying a sample gas generated from a body fluid to be examined collected from an animal, and a second gas flow path for supplying a purge gas not containing a gas component to be measured, wherein the sample gas supplied from the first gas flow path and the purge gas supplied from the second gas flow path are alternately switched and supplied to the at least one surface stress sensor to generate a signal from the at least one surface stress sensor, thereby determining ketosis of the animal based on a composition of the gas generated from the body fluid.

[20] The apparatus for determining ketosis according to [19], further comprising an additional gas sensor and an additional gas flow path for supplying the sample gas to the additional gas sensor, wherein the determination of ketosis is performed based on the signal from the at least one surface stress sensor and the signal from the additional gas sensor.

[21] A apparatus for determining ketosis including: at least one surface stress sensor, a first gas flow path for supplying a sample gas generated from a body fluid to be examined collected from an animal, a second gas flow path for supplying a purge gas not containing a gas component to be measured, and a third gas flow path for supplying a predetermined reference gas, wherein the sample gas supplied from the first gas flow path, the purge gas supplied from the second gas flow path, and the reference gas supplied from the third gas flow path are switched in a predetermined order and supplied to the at least one surface stress sensor to generate a signal from the at least one surface stress sensor, thereby determining ketosis of the animal based on a composition of the gas generated from the body fluid.

[22] The apparatus for determining ketosis according to [21], further comprising an additional gas sensor and an additional gas flow path for supplying the sample gas to the additional gas sensor, wherein the determination of ketosis is performed based on the signal from the at least one surface stress sensor and the signal from the additional gas sensor.

Advantageous Effects of Invention

According to the present invention, it is possible to determine ketosis of an animal based on a composition of a gas generated from a body fluid such as milk obtained by lactation of the animal as a sample to be examined.

Therefore, according to the present invention, it is possible to provide a method capable of easily determining the presence or absence of ketosis and/or the possibility of ketosis of the animal on site or the like with a high throughput and low cost by a method in which a load and stress applied to the animal at the time of specimen collection are small in many cases.

Furthermore, according to the present invention, it is also possible to provide an apparatus for performing the determination.

DESCRIPTION OF EMBODIMENTS

Figure 1:
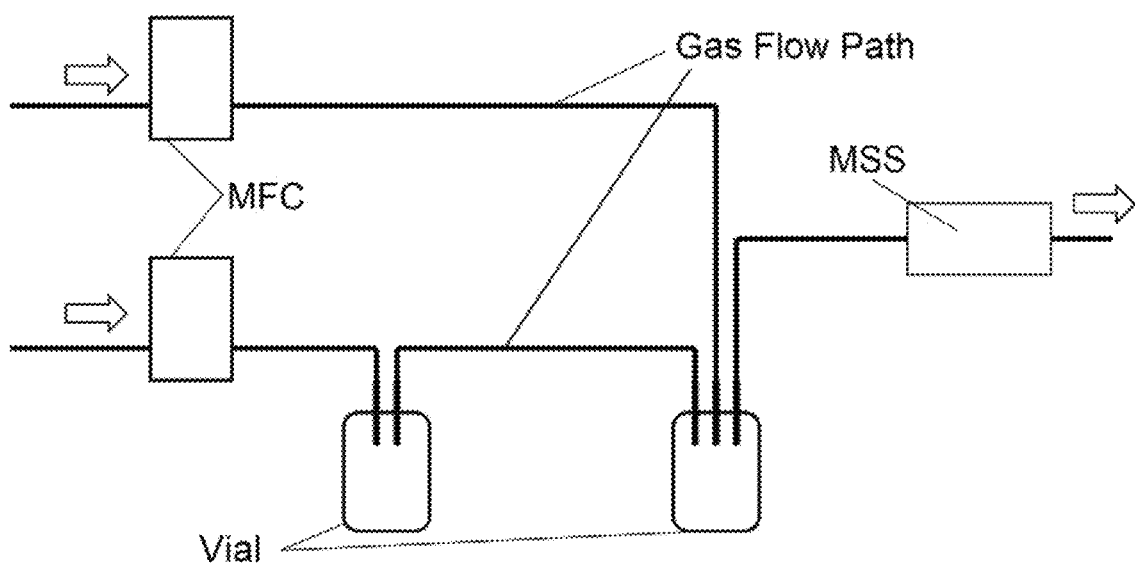
FIG. 1 is a diagram showing a schematic configuration of a measurement system that can be used in the present invention.

Hereinafter, embodiments of the present invention will be described in detail.

The description of components described below may be made based on representative embodiments of the present invention, but the present invention is not limited to such embodiments. Furthermore, a case where milk is exclusively used as the sample to be examined will be described below, but in a case where other body fluids collected from an animal, for example, blood, or other body fluids reflecting a change in a component in blood, such as saliva, urine, or sweat, is obtained in an aspect convenient for the test, these body fluids can also be used. As for the blood, when it is necessary to collect the blood for other tests, it is possible not to impose an additional burden on the animal by diverting a part of the blood. Furthermore, in a case where an apparatus and a collection method capable of collecting blood from an animal in a simple and extremely less painful manner have been established, it is considered that usefulness of utilizing the gas generated from blood as a sample to be examined for determination of ketosis will be further enhanced. In addition, with respect to urine, in recent years, there has been an increasing interest in suppressing generation (volatilization) of ammonia from a livestock barn feeding dairy cows and the like, and an apparatus for collecting urine has been developed from a viewpoint of more appropriate waste urine treatment, and attempts have been made to utilize the collected urine as an alternative to chemical fertilizers. Therefore, it is possible not to impose an additional burden on the animal by diverting a part of the urine.

A method for determining ketosis according to one embodiment of the present invention (hereinafter, also referred to as a "method of the present embodiment") includes providing gas detection means with a gas generated from milk to be examined in which an animal has lactated, and determining ketosis of the animal based on a composition of the gas generated from the milk using a response of the gas detection means to the gas generated from the milk.

The method of the present embodiment is applied to an animal that secretes milk. Examples of the animal include livestock (industrial animals) such as dairy cows, beef cows, goats, sheep, buffalo, yaks, and horses, but are not limited thereto. More preferably, the method of the present embodiment is used for diagnosis of ketosis or as a diagnostic aid of an animal fed for producing milk. In addition, the method of the present embodiment can also be applied as an aid for diagnosis of a disease associated with ketosis in humans.

In the present description, the "gas generated from the milk" refers to a gas component volatilized/evaporated from the milk under a certain environment, that is, volatilized components/evaporated components of the milk. The volatilized components/evaporated components include both an odor component sensed by human sense of smell and a non-odor component not sensed by human sense of smell. Furthermore, note that it is not intended to classify the gas generated from the milk to be examined by the method of the present embodiment according to the presence or absence of odor, and it is not intended to limit to any of them, since the human sense of smell has a very large individual difference and a perceptible component varies greatly from human to human. In addition, when a body fluid other than milk is used as the target to be examined, the gas generated from the body fluid is intended to be obtained by replacing the "milk" in the definition above with the body fluid.

Specifically, examples of the gas generated from the milk include ketones such as acetone; alcohols such as methanol, ethanol, propanol, and butanol; aldehydes such as formaldehyde and acetaldehyde; nitriles such as acetonitrile; organic acids such as formic acid, acetic acid, propionic acid, and butyric acid; and water (water vapor), nitrogen, oxygen, carbon dioxide, and the like. Furthermore, according to a preliminary experiment by the present inventors, from the results of proton transfer reaction time-of-flight mass spectrometry (PTR-TOF-MS) of milk of a healthy cow and a cow suffering from ketosis, the gas generated from the milk may include 2-butanone, butanal, 2-methoxy-1-propene, 2-methylpropanal, and the like in addition to the above substances.

Ketone bodies contained in milk include acetoacetic acid, β-hydroxybutyric acid, acetone, and the like, but acetone has very high volatility, and therefore is not a target to be measured in a test using a liquid as a specimen in the prior art, and β-hydroxybutyric acid and/or acetoacetic acid is used. On the other hand, in the method of the present embodiment, since the gas generated from the milk is used as the specimen, the ketone bodies to be measured are not limited to β-hydroxybutyric acid and acetoacetic acid, and acetone can also be included. In addition, β-hydroxybutyric acid and acetoacetic acid are precursors of acetone, and there is a correlation between the concentrations of β-hydroxy-butyric acid, acetoacetic acid, and acetone in the sample. Therefore, in animals suffering from ketosis, all the concentrations increase. Therefore, in the method of the present embodiment, it is possible to determine ketosis using the acetone concentration in the gas generated from the milk as an index.

In the method of the present embodiment, the gas detection means is not particularly limited, and any means capable of detecting gas generated from milk, such as a gas sensor, a gas chromatograph, and a test paper for gas analysis, may be used. In one aspect of the method of the present embodiment, the gas detection means is a gas sensor, and the response of the gas detection means is signals output from the gas sensor. In this aspect, the determination of ketosis is performed based on the pattern of temporal changes in the signals. Furthermore, in this aspect, prefer-ably, the gas sensor is a surface stress sensor, and more preferably, the surface stress sensor is a Membrane type Surface stress Sensor (MSS). Hereinafter, in order to facili-tate understanding of the present invention, among aspects in which the gas detection means is a gas sensor, an aspect in which the gas sensor is a surface stress sensor will be described as an example.

By selecting an appropriate sensitive film material, the surface stress sensor can obtain response signals (also referred to as signals) for a plurality of target substances from one sensitive film in a form in which the response signals are superimposed. In other words, by appropriately selecting the sensitive film materials for the plurality of target substances, the amplitudes and response waveforms can be made different from each other in the response of the surface stress sensor to each target substance. Accordingly, by combining a plurality of surface stress sensor outputs, it is possible to obtain a measured value in which parameters corresponding to a plurality of target substances are appro-priately combined. At this time, by performing pattern matching and machine learning of the outputs of the surface stress sensors, it is possible to appropriately extract features from these outputs and to realize ketosis determination based on a larger number of parameters than the number of surface stress sensors only by using a relatively small number of surface stress sensors. Naturally, although not limited to this, in a case where another kind of gas sensor particularly convenient for detecting a specific component that is present in the gas generated from the target to be measured and is useful for the determination of ketosis can be used, such a gas sensor can be used in combination with the surface stress sensor as necessary.

FIG. 1 is a diagram showing a schematic configuration of a measurement system that can be used in a method of the present embodiment. Note that, in FIG. 1, a configuration in which a Membrane type Surface stress Sensor (MSS) is used as the surface stress sensor is shown, but naturally, this does not lose generality.

In the schematic configuration shown in FIG. 1, instead of a gas component that should be measured, an inert gas (also referred to as a purge gas or a reference gas) that has the minimum effect on the measurement of such a gas compo-nent is supplied to each of the two gas flow paths as indicated by outlined arrows from the left side of the diagram. As the purge gas, for example, a nitrogen gas or an atmospheric air can be used, and in the examples to be described later, the nitrogen gas is used as the purge gas.

Furthermore, when a simple measurement is performed using an atmospheric air or the like as a purge gas, there is a possibility that a gas that may affect the determination of ketosis, such as an organic acid or ammonia generated from the feeding, is slightly mixed in the atmospheric air at a measurement site (a farm or the like). In such a case, if influence of such a mixed concentration of gas on the result of disease determination does not adversely affect realiza-tion of an intended measurement accuracy (such case is referred to as "substantially not containing a component that affects the determination of ketosis"), such mixing of gas can be ignored. The flow rates of the gas flows of the two systems are controlled by a mass flow controller (MFC) provided for each gas flow path. Specifically, the gas flows in the two gas flow paths are alternately switched at a desired time interval, and the gas flow rate is controlled to be constant on the time axis. Additionally, as a matter of course, the gas flow control is not limited to the MFC, and a system in which various pumps, valves, and the like are combined may be used. At this time, it goes without saying that positions at which the pumps and the valves are arranged may be upstream or downstream of the samples, respec-tively, and may be configured in any order including the positions of the samples and the sensors.

In FIG. 1, the gas flow path shown on the upper side performs purge treatment for initializing the MSS by des-orbing various gases diffused in the sensitive film applied to the surface of the MSS by supplying a purge gas not containing a gas component that should be measured to the MSS. On the other hand, the gas flow passing through the gas flow path on the lower side of FIG. 1 is supplied to the MSS in a state of containing a gas component volatilized/evaporated from the sample in a vial arranged immediately after the MFC. Naturally, in a case where the sample is gaseous from the beginning, or in a case where the gas volatilized/evaporated from a liquid sample is given to the measurement system, a configuration not using the vial can be adopted. The gas flows from the two gas flow paths are joined in another vial and then supplied to the MSS.

Since the rate of gas adsorption/desorption by the sensi-tive film on an MSS surface is affected by temperature, it is preferable to maintain the temperature of the measurement system shown in FIG. 1 at a desired value. As a means for this, for example, the entire measurement system may be contained in a thermostatic chamber, an incubator, or the like, or the MSS and its peripheral components (hereinafter, these are also referred to as "sensor modules" or simply "modules") may be contained in an incubator or the like, and the temperature of the measurement system may be main-tained at the desired value in a state where the vial contain-ing the sample is arranged outside the incubator or the like. In the latter configuration, in a case of measuring a plurality of samples, replacement work of a vial can be performed outside the incubator containing the sensor module or the like, and thus there is an advantage that maintenance and management of the temperature of the measurement system (in particular, the sensor module) is relatively easy as compared with the former configuration. In other words, the former configuration is more suitable for the case of mea-suring a single sample, and the latter configuration (herein-after, also referred to as an "open system") is more suitable for the case of measuring a plurality of samples. In addition, in the examples to be described below, there is an example that the measurement was performed with the entire mea-surement system contained in the incubator as well as an example as the open system.

It is also preferable to maintain the temperature of the vial containing the sample at the desired value in FIG. 1. As a result, it is possible to reduce a variation in the concentration of the gas component volatilized/evaporated from the sample, and to further improve the measurement accuracy. In this case, the temperature of the vial may be the same as or different from the temperature of the measurement system described above. Specifically, examples of a set value of the temperature of the vial include, but are not limited to, 5° C., 10° C., 20° C., 25° C., 30° C., 40° C., and 50° C.

In addition, the present system includes an information processing unit that realizes an evaluation method to be described below by controlling operations of various apparatus in the system such as the MFC, and performing various processes such as capturing, recording, and analyzing the signals from the surface stress sensor, and further includes an interface and a communication unit for exchanging information, commands, and the like, with an external unit or the like, which are omitted in the drawings.

Figure 2:
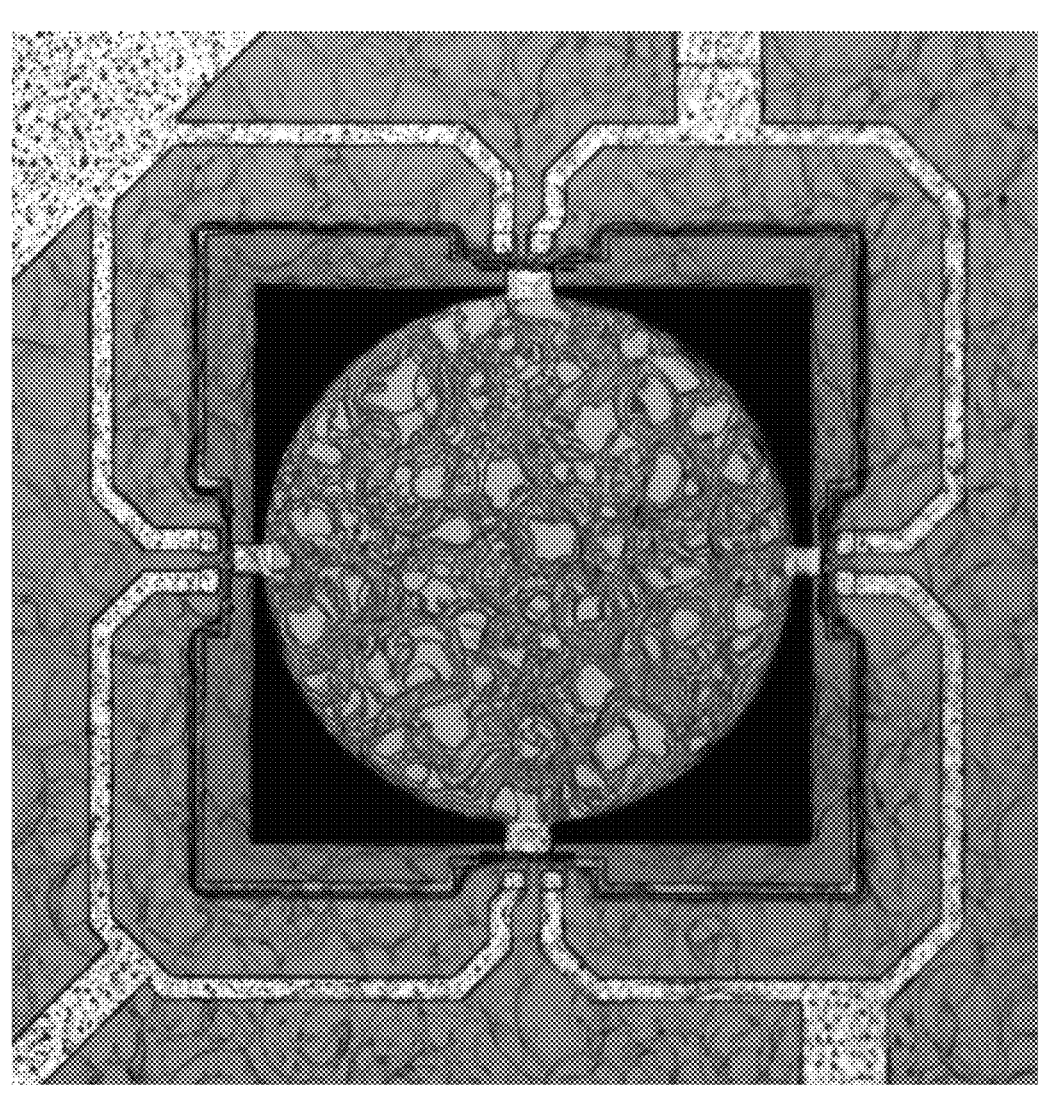
FIG. 2 is an illustration showing an example of an optical microscope photograph of an MSS.

An example of an optical microscope photograph of the MSS is shown in FIG. 2. The MSS shown in FIG. 2 is formed of a silicon wafer cut out from a silicon single crystal, which is used in a field of semiconductor element technique, and a central circular portion thereof (which may have another shape such as a square) is connected and fixed to a surrounding frame-shaped portion thereof at four positions of the circular portion, that is, upper, lower, left, and right positions. The gas component applied to the MSS is adsorbed to and desorbed from the sensitive film applied to the surface of the circular portion, whereby the surface stress applied to the MSS is concentrated on these four fixed regions, leading to a change in electric resistance of piezoresistive elements provided in these fixed regions. These piezoresistive elements are interconnected by conductive regions (shown as sand-grain regions in FIG. 2) provided in the frame-shaped portion to form a Wheatstone bridge. A voltage is applied between two opposing nodes of the Wheatstone bridge, and a voltage appearing between the remaining two nodes is extracted to the outside of the MSS as signals output from the MSS and a required analysis is performed. A structure and operation of such MSS are described in detail in, for example, Patent Literature 1. In FIG. 2, the sensitive film is widely applied to the surface of an MSS chip including not only the circular portion of the MSS but also the frame-shaped portion. This is a state seen when the sensitive film is applied by spray coating, but since the sensitive film applied to the frame-shaped portion or the like does not substantially contribute to sensor output signals, the sensitive film can be used as a sensor without any problem even when applied in this manner. Of course, it is also possible to use an MSS in which the sensitive film is applied only to a circular portion by an inkjet, a dispenser, or the like.

Figure 3:
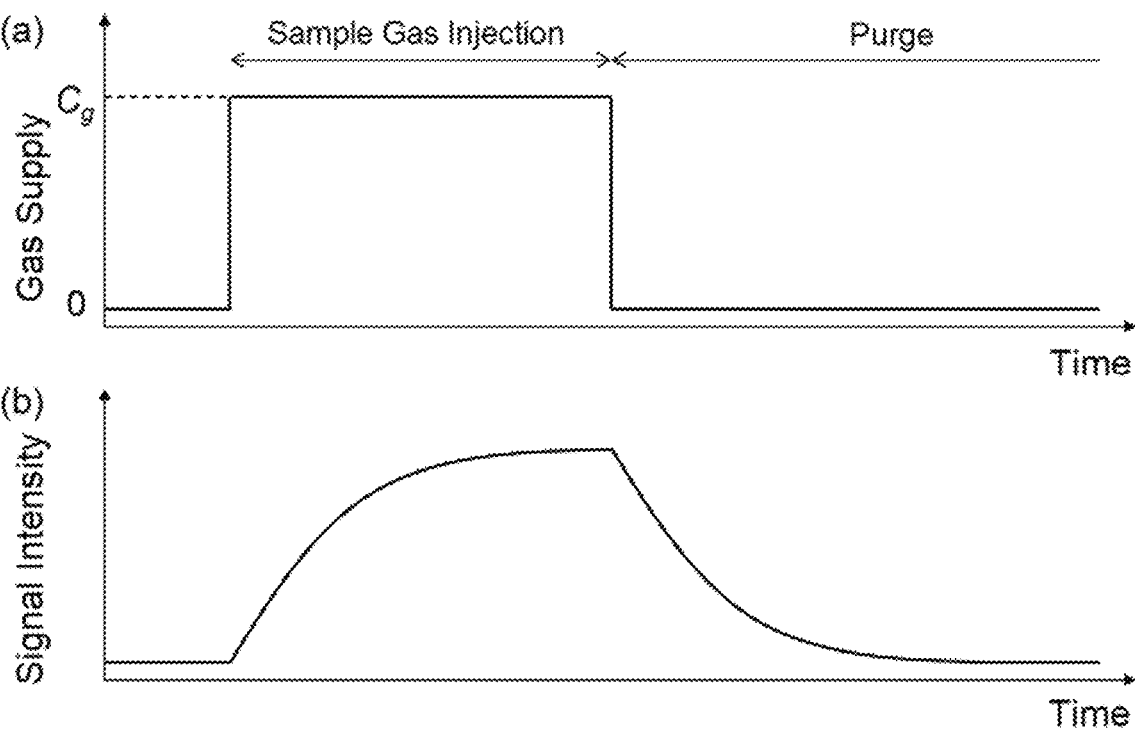
FIGS. 3(a) and (b) are conceptual diagrams for explaining temporal changes in signal intensity when a sample gas is applied to a surface stress sensor such as an MSS.

FIG. 3 shows a conceptual graph of a temporal change in signal intensity when the sample gas is applied to the surface stress sensor such as the MSS. FIG. 3(*a*) shows whether the gas supplied to the MSS is the sample gas or the purge gas on the time axis. Specifically, the concentration of the gas to be measured in the gas supplied to the MSS is a concentration $C_g$, larger than 0, during a sample gas injection period in which the sample gas is supplied, and the sample gas concentration is 0 during a purge period in which a purge operation is performed to flow path the sample gas in a downstream gas flow path by suppling the purge gas and to desorb the sample gas component adsorbed to the sensitive film of the MSS (and a pipe wall or the like of the gas flow path). FIG. 3(*b*) shows the signal intensity from the MSS when the gas kind shown in FIG. 3(*a*) is switched, with the time axis aligned with that of FIG. 3(*a*). Although the signal intensity is governed by many factors, basically, the main factor is a rate of adsorption/desorption of the component between the gas and the sensitive film caused by the difference between the component concentration in the gas in the vicinity of the sensitive film on the MSS and the concentration of the same component on the sensitive film surface. Therefore, temporal change in the signal intensity starts immediately after gas switching shown in FIG. 3(*a*) and becomes close to a curve that asymptotically approaches upper and lower saturation values exponentially. FIG. 3(*b*) shows the curve in an ideal case. The actual shape of the curve, the maximum value of the curve, and the like, change considerably depending on the rate of adsorption to/desorption from the sensitive film and the kind of the component adsorbed to/desorbed from the sensitive film, and a change range of the signals is also greatly different in many cases. Furthermore, the signals can show a more complicated temporal change due to viscoelastic property of the sensitive film, diffusion of the gas to be measured into the sensitive film, the physicochemical interaction between the sensitive film material and the gas to be measured, or the like. In this manner, the amount and concentration of each main component in the sample, the ratio between the plurality of components, and the like, can be obtained based on the temporal change, the amplitude, and the like, of the signals from the MSS. Specifically, among gases generated from milk, there is a sensitive film material that gives signals suitable for measurement of ketones, and there is also a sensitive film material that gives signals suitable for measurement of alcohols. Accordingly, the determination based on the composition of the gas generated from the milk can be performed by measuring the gas generated from the milk using the surface stress sensor to which a material appropriately selected from these materials is applied alone, or performing the same measurement using a plurality of kinds of surface stress sensors to which different materials are respectively applied.

Here, materials forming the sensitive films have various adsorption/desorption characteristics, and there are also sensitive film materials showing a response deviating from the simplified model described above. However, it can be said that, when analyzing the response of the surface stress sensor or on other occasions, performing the first examination using the above model is useful in many cases.

Although FIG. 3 shows that the sample gas is supplied to the MSS only once, in the measurement using the surface stress sensor such as the MSS, it is common to repeat the measurement as shown in FIG. 3 over a plurality of times by alternately switching and supplying the sample gas and the purge gas. Hereinafter, the set of sample gas injection followed by purge is referred to as a measurement cycle (details will be described later). Moreover, in many cases, the sample gas injection period and the purge period have the same time length unless there is a circumstance such as a large difference between the adsorption rate and the desorption rate of a certain component in the sample gas, but it is natural that the sample gas injection period and the purge period may have different time lengths.

Usually, since the gas generated from the milk to be examined is a trace component in the milk, it may take a relatively long time to obtain an effective signal value among sensor signals generated along with adsorption and desorption of the gas component to and from the sensor. Furthermore, in a case where a component that is difficult to be desorbed remains in the sensor, reproducibility of the signal value of the sample gas to be measured next may be lowered. Therefore, in the present aspect, it may be effective to set the sample gas injection period and the purge period in one measurement cycle to different lengths, and it is preferable to set the purge period to be longer than the sample gas injection period after securing a sufficient time to obtain the signal value efficient for the sample gas injection period. Specifically, in the examples to be described later, the sample gas injection period is set to 120 seconds, and the purge period is set to 240 seconds, which is twice the sample gas injection period. Furthermore, by setting one measurement cycle as a measurement sequence of "purge period to sample gas injection period to purge period", it is also effective to perform purge substantially twice before the second and subsequent sample gas injections when performing measurement for a plurality of times. Also in the examples to be described later, by adopting this measurement sequence, a purge period of 480 seconds (240 seconds+240 seconds) from the end of the most recent sample gas injection is secured before the second and subsequent sample gas injections. As described above, by lengthening the purge period with respect to the sample gas injection period, the components adsorbed on the sensitive film on the MSS during the sample gas injection are easily desorbed sufficiently, and a baseline can be more stabilized. Therefore, it is particularly effective to secure determination accuracy when the measurement is repeated for a plurality of times.

In other words, when the purge period is shorter than the sample gas injection period, the determination accuracy may be adversely affected. In actual measurement, an increase in measurement time causes not only inconvenience such as a decrease in measurement throughput, but also causes a problem that it is often difficult to stabilize various parameters (the flow rate, gas pressure, temperature, and the like) of environment inside and outside the measurement system for a long time, or a problem of an increase in size and price of the measurement system. Furthermore, since the measurement system usually includes active components such as a pump, a temperature change over a long period of time due to heat generated from the active components may also adversely affect the determination accuracy. Accordingly, in the present aspect, it is desirable that the time of the measurement cycle is distributed as short as possible within a range in which the effective signal value can be obtained in the sample gas injection period (sampling time), and the purge period (purge time) is made as long as possible. Alternatively, as a countermeasure in a case where the baseline fluctuation becomes a problem, a reference milk (details will be described later) in which the amount of components that can affect the determination accuracy is a predetermined value is prepared, and an adverse effect due to purge for a short time can be eliminated or reduced by measuring a gas generated from the reference milk for each measurement and performing calibration.

As described above, in the measurement system having the schematic configuration shown in FIG. 1, usually, the gas flows in the two gas flow paths are alternately switched at desired time intervals, and the gas flow rate is controlled by the MFC (or the pump or the like) so as to be constant on the time axis. However, depending on a configuration of the measurement system, a specification of the gas detection means (the MSS in FIG. 1), and the like, it may be possible to further stabilize the baseline by making the gas flow rate during the purge period larger than the gas flow rate during the sample gas injection period.

In the present aspect, the determination of ketosis of the animal based on the composition of the gas generated from the milk is performed using the measurement result (hereinafter, it is also simply referred to as the "measurement result") of the temporal changes of the signal intensity as shown in FIG. 3, which is obtained by applying the sample gas to the surface stress sensor such as the MSS.

Specifically, the measurement result may be used as it is, or any data analysis processing may be performed on the measurement result. For example, a time point arbitrarily selected from the time range of the measurement cycle is set as a reference point, and an offset treatment is performed with this time point as a reference. Thereafter, the presence or absence of ketosis and/or the possibility of ketosis can be determined by obtaining the feature value from a determination point or a value in the vicinity of the determination point using another arbitrary time point from the above time range as the determination point. The feature value may be, for example, the signal intensity after the offset treatment at the determination point, a slope of the graph of the signal at the determination point, an average slope or curvature of the graph of the signal in the vicinity of the determination point, or the like. Note that, since a raw signal on which the offset treatment of the signal is not performed includes unique information such as a long-term temporal change of the sensor and a current state as an absolute value of the sensor signal, values of the raw signal may be used as it is or an arbitrary feature value may be extracted from the raw signal and analyzed without performing the offset treatment.

Here, the offset treatment is processing of obtaining the signal intensity $S'(t)=S(t)-S(t_0)$ after the offset treatment by translating the graph of the signal intensity in an intensity axis direction so that the signal intensity $S(t_0)$ at the reference point to becomes 0 (generally, an arbitrary constant).

Examples of the reference point include a time point immediately before a start of the sample gas injection period (that is, an end of the purge period) and a time point immediately before a start of the purge period (that is, an end of the sample gas injection period), but any other time point may be used. However, since the gas to be applied to the surface stress sensor is switched at the time of switching between purge and injection, the signal from the surface stress sensor may be disturbed in the vicinity of this boundary point. In addition, even when the switching is performed, there may be a time delay that cannot be ignored until the gas around the surface stress sensor at a position passing through the gas flow path of a certain length from a switching mechanism such as a valve is actually switched. In a case where the influence of instability or time delay such as the signal disturbance can be a problem, a time point slightly shifted in time from the time point of this switching may be adopted as the reference point.

In addition, a time point arbitrarily selected from the time range of the measurement cycle is set as the reference point, and the offset treatment is performed based on the selected time point. Thereafter, the presence or absence of ketosis and/or the possibility of ketosis can be determined by obtaining the feature value from the determination point or a value in the vicinity of the determination point using another arbitrary time point within the above time range as the determination point. The feature value may be, for example, the signal intensity after the offset treatment at the determination point, the slope of the graph of the signal at the determination point, the average slope or curvature of the graph of the signal in the vicinity of the determination point, or the like. When an offset amount of the signal is sufficiently small or the feature value obtained from the signal intensity before the offset is sufficiently large, the offset treatment may be omitted. However, the determination point satisfying such conditions may vary depending on not only the time length of the measurement cycle and the time lengths of the sample gas injection period and the purge period, but also the configuration of the measurement system (the gas flow path, a gas supply mode to the measurement system, a gas flow rate, and the like) and measurement conditions, and furthermore, the kind of sensitive film material and the like, in a case where the gas detection means is a surface stress sensor (more specifically, an MSS). Therefore, it is desirable to confirm in advance a combination of the reference point and the determination point at which the feature value effective for the determination of ketosis can be extracted for each sensitive film material using the reference milk or the like.

As described above, in the present aspect, by appropriately setting time allocation of the measurement cycle and the configuration of the measurement sequence, it is possible to suppress the fluctuation of the baseline and stabilize the baseline, and thus, it is possible to secure the determination accuracy even when the difference in the extracted feature value is minute. Specifically, since the gas is sufficiently desorbed from the sensitive film by lengthening the purge period, it is possible to return the state before the sample gas injection to the same state every time. In other words, lengthening the purge period is useful for sufficiently resetting the measurement system. The time point when the reset is sufficiently performed is the time point immediately before the sample gas injection, and signal reproducibility is secured by using this time point as the reference point of the offset, and as a result, highly accurate determination is facilitated. Moreover, in particular, by performing offset treatment with reference to the signal at the time of purging immediately before the start of sample gas injection and setting the determination point at a time point when a slight time has elapsed from the end of the injection period, the fluctuation in the signal intensity at the determination point is more likely to become clear, and the feature value effective for the determination of ketosis is likely to be obtained. In experiments shown in the examples, by observing the signal intensity at the time point of several seconds to tens of seconds after the end of the injection period or the change in the signal intensity in the vicinity of the time point, the determination by visual observation becomes the easiest.

In the above description, the measurement based on the measurement sequence for switching between the sample gas and the purge gas is performed, but the present invention is not limited thereto. For example, a measurement for another gas (the reference gas) containing a component that is contained in the sample gas and whose concentration may affect the determination of ketosis can be inserted into the measurement sequence to perform the determination of ketosis based on signals from a switching measurement of the three kinds of gases.

As such reference gas, milk obtained from a healthy animal not suspected of suffering from ketosis may be used as the reference milk, and a gas having the same component composition as the sample gas component generated from the reference milk may be used as the reference gas. Such reference milk may be, for example, obtained from an animal (hereinafter, the animals are also referred to as "animals in the same group") belonging to the same breeding environment as the animal to be examined, and in this case, the milk may be individual milk (milk obtained from a single individual animal. milk obtained from an animal known to be healthy among animals of the same group is preferable), and may also be a milk mixture (milk obtained by mixing a plurality of milks from individuals in a breast expression tank or the like, and also called bulk milk).

Alternatively, various compositions can be set as necessary, in such a manner that a gas having the same composition for some components (for example, a component for which a slight difference in component amount is desired to be measured with particularly high accuracy) of the sample gas assumed as described above may be used as the reference gas or the like. Then, a supply sequence of these three kinds of gases is appropriately set in consideration of various requirements, restriction conditions, and the like in the measurement. For example, the measurement sequence including repetitions of a gas supply time frame as follows is considered:

A. Supply the purge gas→[supply one of either the sample gas or the reference gas→supply the purge gas→supply the other gas (the sample gas or the reference gas)→supply the purge gas](or repeat the sequence within the square brackets [ ])

B. Supply the purge gas→[alternately supply the sample gas and the reference gas→supply the purge gas](or repeat the sequence within the square brackets [ ])

C. Supply the purge gas→[repeat alternate supply of either one of the sample gas or the reference gas, and the purge gas→supply the purge gas→repeat alternate supply of the other gas (the sample gas or reference gas) and the purge gas](or repeat the sequence within the square brackets [ ])

Other than these, various gas supply sequences for the gas supply time frames are also possible. In any gas supply sequence, since it is considered that measurement conditions such as temperature, gas pressure and flow rate, and the temporal change in sensor characteristics do not greatly change in a series of measurement sequences, it is possible to accurately measure a slight difference in composition between the sample gas and the reference gas by comparing the two, and it is also possible to improve measurement stability such that, for example, an influence of disturbance on a measurement result can be reduced.

In a case of having to use the reference gas, a gas flow path for the reference gas is added to a gas supply system of a measuring apparatus, but this can be easily realized using various existing techniques for the gas supply system. For example, the reference gas can be prepared in a gaseous state from the beginning, or may be introduced into the gas supply system by being evaporated from a liquid or a solid. Moreover, when the reference gas is provided, another gas such as the purge gas may be mixed with the initially prepared gas or the gas generated from the liquid or solid. Additionally, these three gas flow paths of the system need to be finally joined. The three flow paths may be joined at one place, or the gas flow paths may be configured such that an upstream side of the sample gas flow path is partially divided to form a reference gas flow path, the reference gas is introduced into the reference gas flow path, and then both gas flow paths are joined before a junction with the purge gas.

Furthermore, in a case where the reproducibility of the measurement is high as long as the required determination accuracy can be realized and the variation between a sensor chip and a measurement unit can be calibrated, the measurement of the sample gas and the measurement of the reference gas can be made independent of each other, and a measurement procedure performed at different convenient time points and a measurement system therefor can be constructed. For example, the measurement of the reference gas and the measurement of the sample gas may not be performed simultaneously or sequentially in a series of measurement sequences, but may be performed separately, and reference gas measurement data and sample gas measurement data obtained from these measurements may be compared. Here, as long as the conditions described above, that is, the conditions that the reproducibility of the measurement is high as long as the required determination accuracy can be realized and the variation between the sensor chip and the measurement unit can be calibrated is satisfied, the sensor chip and the measurement unit used for measuring the sample gas, and the sensor chip and the measurement unit used for measuring the reference gas, may be the same sensor chip and measurement unit, or a sensor chip and a measurement unit different from those used for one of the measurements may be used. Alternatively, the measurement may be performed using only the sample gas and the reference gas without using the purge gas. In this case, the measurement may be performed using the reference gas as the purge gas. Furthermore, the measurement using only the sample gas or only the reference gas is also possible. In this case, by exposing the sample gas or the reference gas to the sensor for a sufficiently long time, each gas is sufficiently adsorbed and diffused to the sensitive film, and it may be waited until the sensor shows a constant signal value. The absolute value of this signal may be used as it is as the feature value, or a signal when exposed to the atmospheric air or the like for a sufficiently long time may be measured before the measurement, and the measured signal may be used as the reference point.

Although not limited to this, for example, in the case of comparing past milk from the same animal with milk of the present breast expression result, it is not realistic to store the past milk itself or volatilized/evaporated components therefrom so as not to deteriorate. Therefore, in a case where the gas obtained from the milk at the time point when it is already known that the animal is healthy in the past is measured and the gas is accumulated as data of the reference gas, the gas obtained from the current milk from the same animal is similarly converted into the data as the sample gas, and as long as the reproducibility of the measurement and a calibration possibility of various variations can be secured, the comparison of the gas in a state in which the milk of each target to be measured is fresh can be realized. In addition, data conversion of the measurement result of each gas is not particularly limited here. As a non-limiting example, an output from the sensor at the time of performing an alternate switching between each gas and the purge gas may be digitized as it is, or a sensor output at the time of measurement of another form may be digitized, or for example, a digital value of the result of the digitization as described above may be further subjected to data treatment.

Examples of the material of the sensitive film of the surface stress sensor include poly(4-methylstyrene), poly(2, 6-diphenyl-p-phenylene oxide), poly(vinylidene fluoride), cellulose acetate butyrate, poly(ethyleneimine), phenyl group-modified silica/titania composite nanoparticles (hereinafter, also referred to as "phenyl-STNPs"), and polystyrene, but are not limited thereto. These sensitive film materials may be used singly or in combination of two or more kinds thereof.

For example, in an aspect in which a gas generated from milk is used as a sample to be examined, among the sensitive film materials, at least one selected from the group consisting of poly(4-methylstyrene), poly(2,6-diphenyl-p-phenylene oxide), poly(vinylidene fluoride), cellulose acetate butyrate, and poly(ethyleneimine) can be used. Among them, it is preferable to use at least one selected from the group consisting of poly(4-methylstyrene), poly(2,6-diphenyl-p-phenylene oxide), cellulose acetate butyrate, and poly(ethyleneimine).

In an aspect in which a gas generated from urine is used as the sample to be examined, at least one selected from the group consisting of poly(4-methylstyrene), poly(2,6-diphenyl-p-phenylene oxide), poly(vinylidene fluoride), phenyl-STNPs, and polystyrene can be used among the sensitive film materials. Among them, it is preferable to use at least one selected from the group consisting of poly(4-methylstyrene), poly(2,6-diphenyl-p-phenylene oxide), and poly(vinylidene fluoride), and it is more preferable to use at least one selected from the group consisting of poly(4-methylstyrene) and poly(2,6-diphenyl-p-phenylene oxide).

In other words, among the sensitive film materials, poly(4-methylstyrene), poly(2,6-diphenyl-p-phenylene oxide), and poly(vinylidene fluoride) are sensitive film materials that can be suitably used for a plurality of kinds of targets to be examined including milk and urine, and in this sense, can be said to be more versatile sensitive film materials.

A specific measurement example using the sensitive film material exemplified above will be described later.

Furthermore, poly(2,6-diphenyl-p-phenylene oxide) is a material also known by the name of "Tenax" (registered trademark), and several kinds of poly(2,6-diphenyl-p-phenylene oxide) are commercially available depending on its purity and additives. Examples thereof include Tenax TA and Tenax GR obtained by adding a suffix to Tenax (Tenax GR is obtained by blending 23% of graphite carbon at the time of Tenax polymerization), and any of these can be used in the method of the present embodiment. Moreover, Tenax having various particle size distributions is provided, and a range of the particle size is represented by a mesh such as Tenax TA 20/35. In addition, in the examples to be described later, Tenax TA 60/80 (available from GL Sciences Inc.) was used as poly(2,6-diphenyl-p-phenylene oxide).

Hereinafter, the present invention will be described in more detail with reference to the examples. It should be noted that the following examples are not intended to limit the present invention but to help understanding thereof.

EXAMPLES

In the examples, the measurement system having a schematic configuration shown in FIG. 1 was used.

The MSS used was actually an aggregate including a plurality of MSS each coated with a different sensitive film material. Hereinafter, among these sensitive film materials, an MSS using poly(4-methylstyrene) is referred to as "ChA", an MSS using poly(2,6-diphenyl-p-phenylene oxide) is referred to as "ChB", an MSS using poly(vinylidene fluoride) is referred to as "ChC", an MSS using cellulose acetate butyrate is referred to as "ChD", an MSS using poly(ethyleneimine) is referred to as "ChE", an MSS using phenyl group-modified silica/titania composite nanoparticles (phenyl-STNPs) is referred to as "ChF", and an MSS using polystyrene is referred to as "ChG".

<Test 1: Measurement of Gas Generated from Milk of a Healthy Cow in Different Breeding Environments>

In the Hokkaido Agricultural Research Center, National Agriculture and Food Research Organization, 10 mL of milk of a dairy cow (a range cow) fed with fresh grass by grazing (sample 1) and 10 mL of milk of a dairy cow (a house cow) fed with silage by housekeeping (sample 2) were contained in vials and measured.

Note that the milk of the sample 1 and the sample 2 had different scents to the extent that discrimination by the human sense of smell was possible, and the milk of the sample 1 and the sample 2 also had a greatly different flavor by the human sense of taste.

The temperature of the incubator containing the measurement system was set to 30° C. The flow rates of the sample gas and the purge gas were set to 10 sccm, and the sampling time (time for performing sample gas injection in each measurement cycle) was set to 120 seconds. Furthermore, the measurement was performed with a ratio of the sampling time to the purge time (the time for supplying the purge gas to the MSS and performing the purge in each measurement cycle) set to 1:4. Specifically, in the measurement sequence in each measurement cycle, the purge gas was caused to flow for 240 seconds first, the sample gas was caused to flow for 120 seconds next, and then the purge gas was caused to flow again for 240 seconds. In other words, since each measurement was continuously performed, the purge gas flowing after flowing the sample gas and the purge gas flowing before flowing the next sample gas continuously flow without interruption. Therefore, the purge time is a sum of the two purge times, and the ratio of the sampling time to the purge time is substantially 1:4. Note that these measurement conditions can be appropriately adjusted according to the configuration of the measurement system.

A procedure for switching the sample (for example, switching to another milk) during the measurement sequence will be described here. After the sampling time, the vial containing the sample was separated from the gas flow path by a switching valve. Accordingly, the sample to be measured can be switched to the next sample at an arbitrary timing without affecting the measurement.

The replacement work of a measurement sample (replacement of the vial and the like) requires tens of seconds, and input work or the like of reflecting that the sample replacement has been performed in data setting or the like of the measurement system is required. Therefore, time for stopping the sensor module is required between two measurements of measuring different samples. However, since a module temperature decreases due to the stop of the sensor module, the baseline fluctuates. Since this baseline variation becomes a large noise in measuring a fine signal difference, it is ideal to suppress a module stop between measurements to be within 1 second. Here, as described above, by separating the vial (of course, the same applies to other kinds of sample storage containers and the like) containing the sample from the gas flow path after the sampling time, replacement of the vial and other work associated with the replacement can be performed while the vial is separated. Accordingly, in such a method, by switching the sample in parallel with the purge treatment, sample switching time can be prevented from substantially appearing on the measurement sequence.

Figure 4:
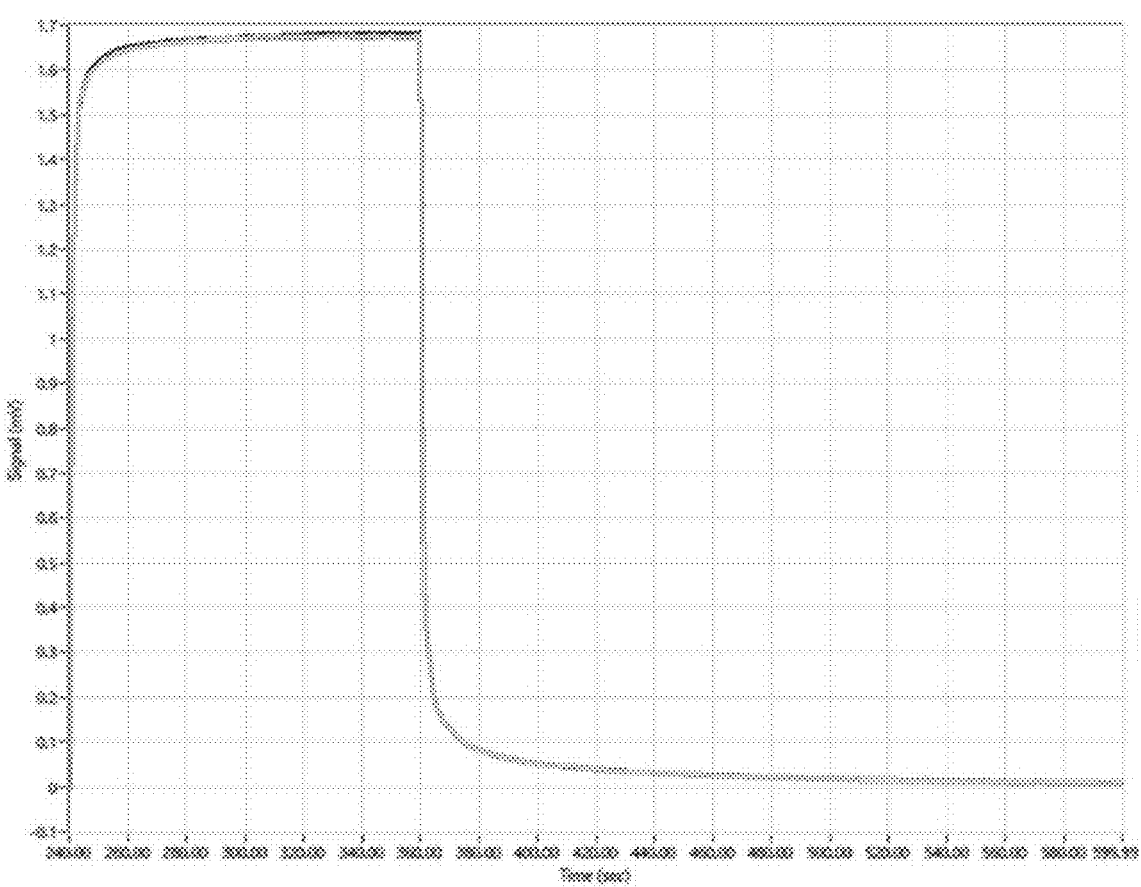
FIG. 4 shows graphs indicating temporal changes (unit: second) of signals (unit: mV) from an MSS of ChA for Test 1 of examples.

The results are shown in FIG. 4.

FIG. 4 shows graphs indicating temporal changes (unit: second) of signals (unit: mV) from the MSS of ChA. In FIG. 4, the measurement result of the sample 1 is shown in light gray, and the measurement result of the sample 2 is shown in dark black.

Furthermore, in the results shown in FIG. 4, a starting point (that is, an end point of a first purge period) of the sample gas injection period of the measurement sequence is set as a starting point of the offset, and a typical result among the results of performing the plurality of measurements on the same sample is plotted. The same applies to FIGS. 5-14 and FIGS. 18-22 to be described later.

As can be seen from FIG. 4, in a case of using the sensitive film material of ChA, in behavior in which the signal intensity sharply rises immediately after the start of the sample gas injection period, and then asymptotically approaches the saturation value, there is a time frame (a range of about 270 seconds to 325 seconds) during which the signal intensity of the house cow is slightly higher than that of the range cow, but there is no difference so that a significant difference can be obtained by extracting some feature values, and time courses of the signals other than the time frame are almost the same. In other words, when the sensitive film material of ChA was used, there was no clear difference as a signal with respect to the gas component detected by the MSS even when the milk has scents or a flavor that is so different that it can be clearly distinguished by human sense of smell or taste. From this, it was suggested that when a different tendency was observed in the temporal changes of the signals from the MSS of ChA, it was highly likely to be caused by a disease of dairy cows.

<Test 2: Measurement of Gas Generated from Milk Simulating Milk of a Cow Suffering from Ketosis>

According to Non Patent Literature 2, the acetone concentration in milk of healthy cows is less than 0.7 mmol/L, whereas the acetone concentration in milk of a cow suffering from hyperketonemia (hyperketonaemia), in which a decrease in milk production is clearly observed, is more than 1.4 mmol/L (see Table 1).

Therefore, it was assumed that the acetone concentration in the milk of the sample 2 (milk of the house cow) used in Test 1 was 0.7 mmol/L, and 0.1 mL of an aqueous solution having an acetone concentration of 70 mmol/L was added to 10 mL of the milk of the same house cow to prepare a sample (sample 3) in which the acetone concentration in the milk approximates 1.4 mmol/L, and this was used as milk imitating the milk of a cow suffering from ketosis. Furthermore, for comparison, a sample (sample 4) in which 0.1 mL of distilled water was added to 10 mL of the milk of the same house cow as used in Test 1 was prepared, and the sample 3 and the sample 4 were each contained in a vial to perform the measurement.

The measurement conditions such as the temperature of the incubator containing the measurement system were the same as in Test 1.

Figure 5:
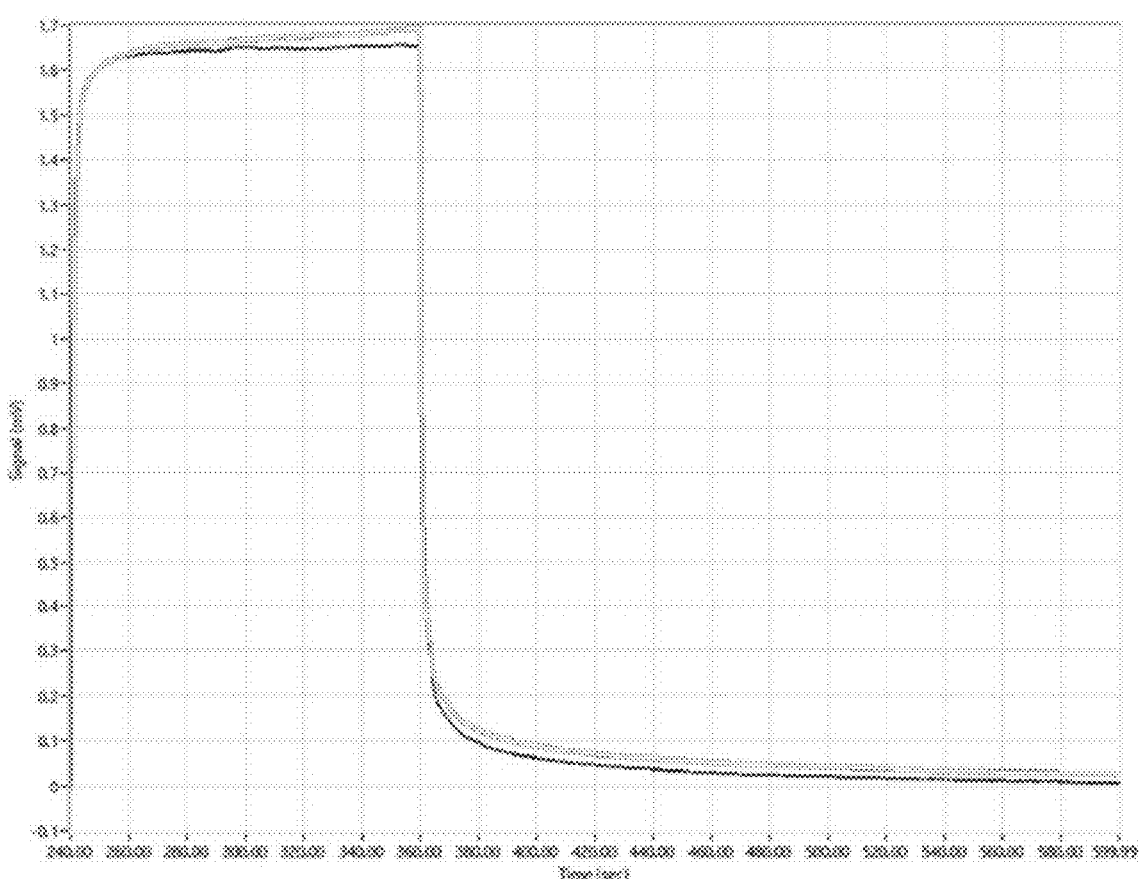
FIG. 5 shows graphs indicating temporal changes (unit: second) of signals (unit: mV) from the MSS of ChA for Test 2 of the examples.

The results are shown in FIG. 5.

FIG. 5 shows graphs indicating temporal changes (unit: second) of signals (unit: mV) from the MSS of ChA. In FIG. 5, the measurement result of the sample 3 is shown in light gray, and the measurement result of the sample 4 is shown in dark black.

As can be seen from FIG. 5, when the sensitive film material of ChA was used, a difference in the temporal changes of the signals was confirmed between the sample 3 and the sample 4. Specifically, the signal intensity sharply rises immediately after the start of the sample gas injection period, and then the behavior of asymptotically approaching the saturation value is different. In addition, there is also a difference in behavior (a tendency of decrease in the signal intensity) from a sharp falling of the signal intensity immediately after switching from the sample gas injection period to the purge period to convergence (return) to the baseline. Furthermore, there is also a difference in the saturation value of the signal intensity. In addition, as compared with the case where the start point of the purge period was set as the starting point of the offset, the difference in the measurement results between the sample 3 and the sample 4 was clearer in the result shown in FIG. 5.

On the other hand, even when the sensitive film materials of ChB, ChD, and ChE were used, a difference in the temporal changes of the signals was confirmed between the sample 3 and the sample 4, but it was not so clear as compared with the case of ChA (data are not shown). It can be said that this suggests a possibility that it is difficult to determine alone based on the measurement result by the MSS of ChB, ChD, or ChE, but it does not deny a possibility that it is possible to determine based on a combination with the MSS using ChA or other sensitive film materials (or other gas detection means including a surface stress sensor of a type different from the MSS).

<Test 3: Measurement (1) of Gas Generated from Milk of a Cow Suffering from Ketosis>

Contained in a vial and measured were each 10 mL of the milk (sample 5) determined to be strongly positive (BHBA concentration: 1000 μM) and 10 mL of the milk (sample 6) determined to be negative (BHBA concentration: 50 μM) by a test using a product (San Keto Paper, SANWA KAGAKU KENKYUSYO Co., Ltd.) for semi-quantifying β-hydroxy-butyric acid in the milk.

In addition, the measurement of the sample 5 and the sample 6 was performed using samples that were left to stand at normal temperature for about 24 hours after breast milk collection.

In the measurement of the sample 5 and the sample 6, the vial was placed in an ambient temperature (about 25° C.) environment, and the measurement system was an open system. During the measurement, the temperature of the sensor module was stable at about 36.5° C.

Other measurement conditions such as the flow rates of the sample gas and the purge gas were the same as in Test 1.

Furthermore, the fact that the dairy cows from which the sample 5 and the sample 6 were collected include those suffering from ketosis and the healthy cow is determined by comprehensively analyzing peak intensities derived from the acetone in mass spectra of a milk sample and a urine sample by PTR-TOF-MS in addition to test results of the milk sample using the above products. The same applies to Test 4 and Test 5 to be described later.

The results are shown in FIGS. 6-9.

Figure 6:
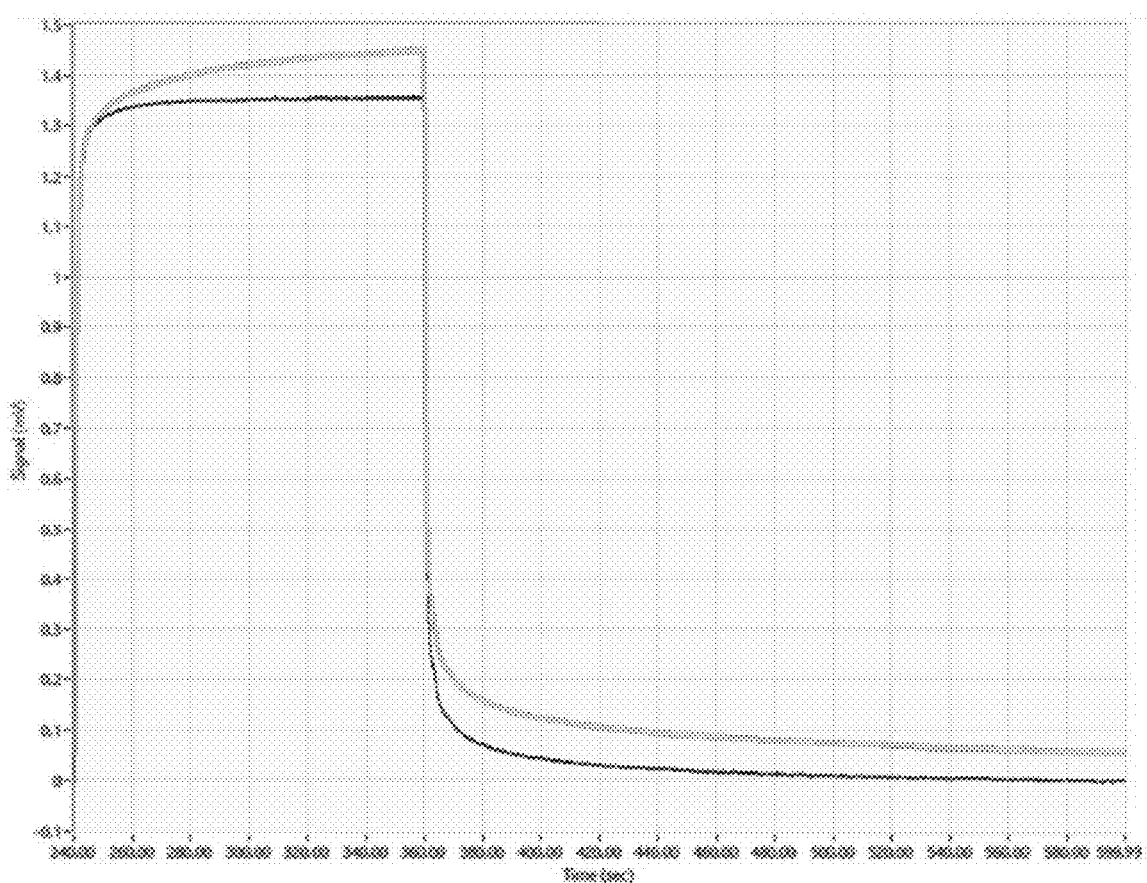
FIG. 6 shows graphs indicating temporal changes (unit: second) of signals (unit: mV) from the MSS of ChA for Test 3 of the examples.

FIG. 6 shows graphs indicating temporal changes (unit: second) of signals (unit: mV) from the MSS of ChA.

Figure 7:
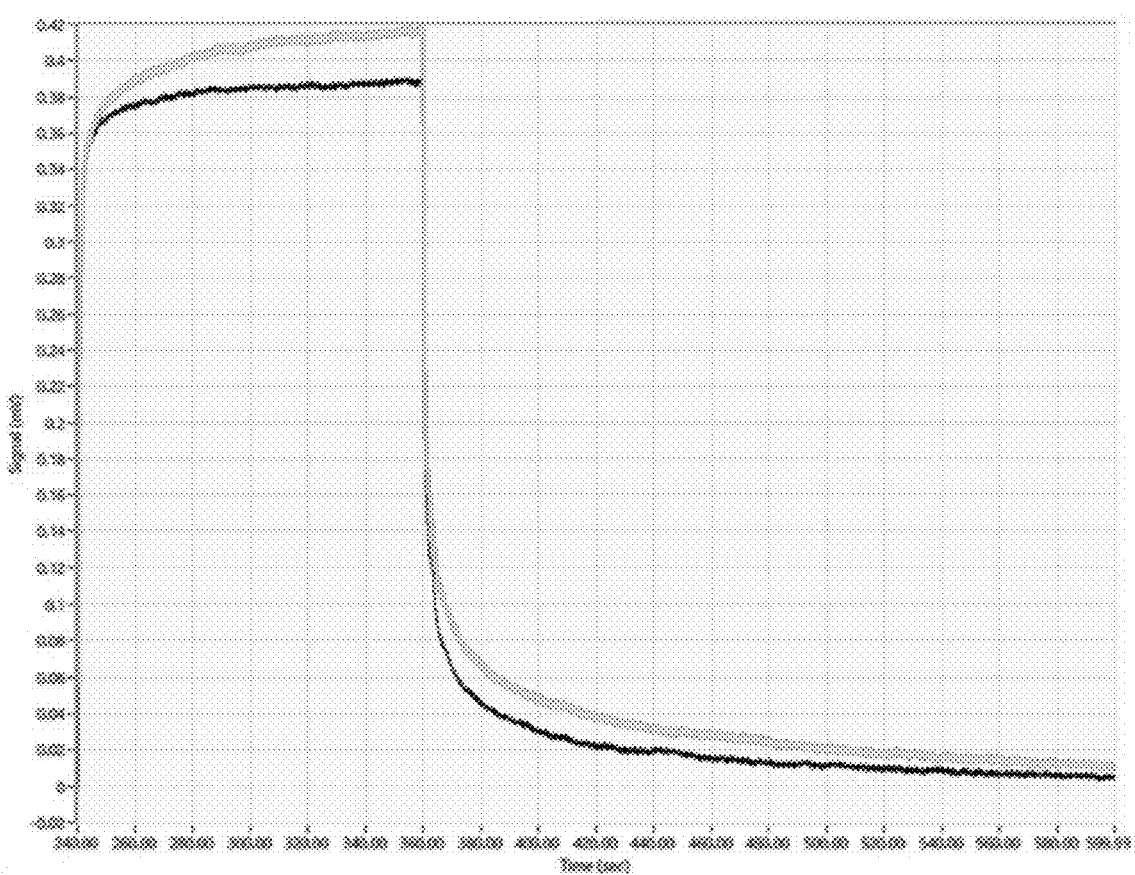
FIG. 7 shows graphs indicating temporal changes (unit: second) of signals (unit: mV) from an MSS of ChB for Test 3 of the examples.

FIG. 7 shows graphs indicating temporal changes (unit: second) of signals (unit: mV) from the MSS of ChB.

Figure 8:
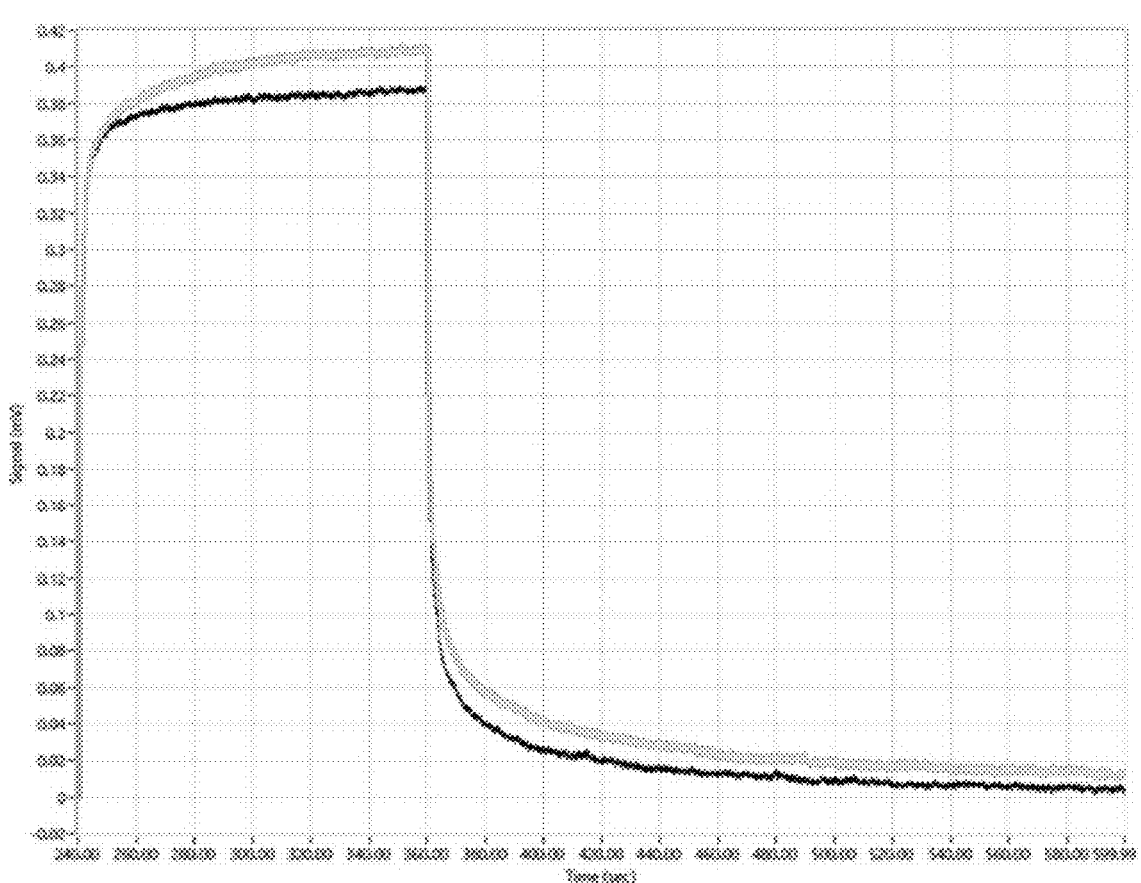
FIG. 8 shows graphs indicating temporal changes (unit: second) of signals (unit: mV) from an MSS of ChD for Test 3 of the examples.

FIG. 8 shows graphs indicating temporal changes (unit: second) of signals (unit: mV) from the MSS of ChD.

Figure 9:
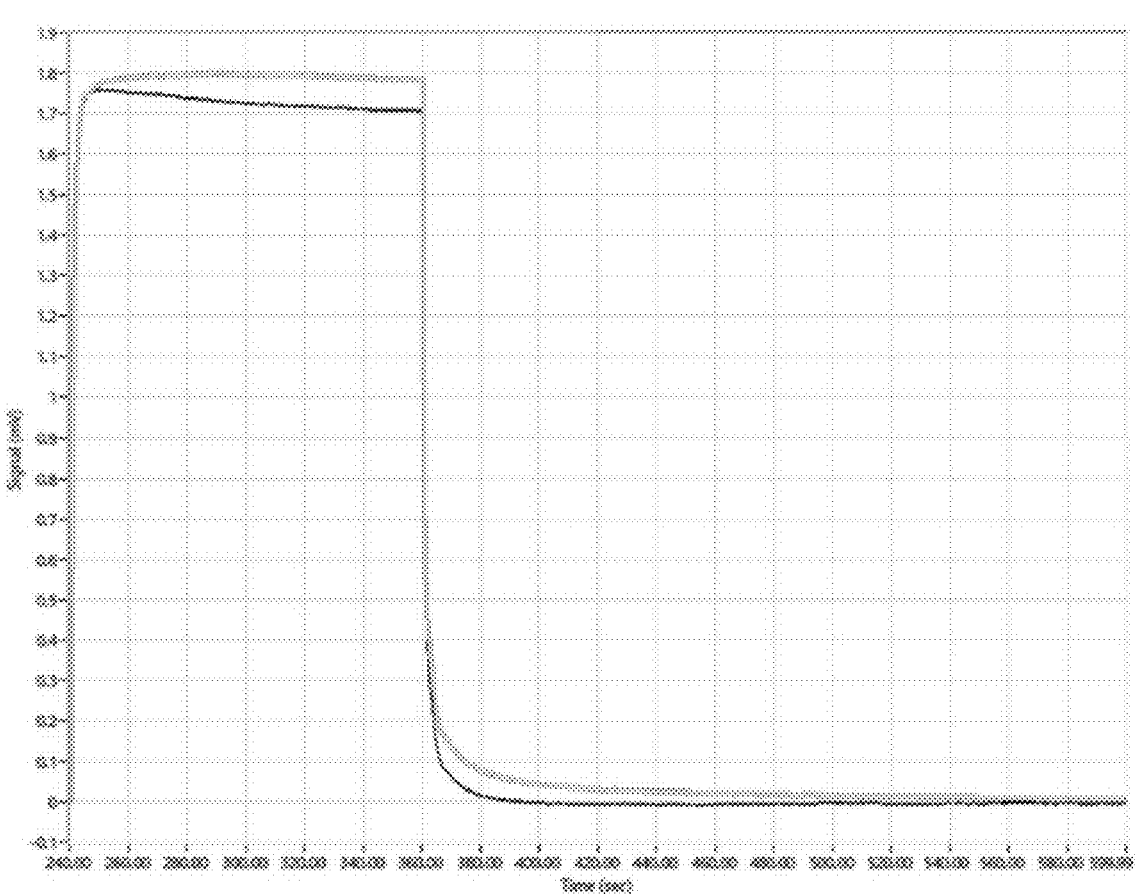
FIG. 9 shows graphs indicating temporal changes (unit: second) of signals (unit: mV) from an MSS of ChE for Test 3 of the examples.

FIG. 9 shows graphs indicating temporal changes (unit: second) of signals (unit: mV) from the MSS of ChE.

In FIGS. 6-9, the measurement result of the sample 5 is shown in light gray, and the measurement result of the sample 6 is shown in dark black.

As can be seen from FIG. 6, when the sensitive film material of ChA was used, the temporal changes of the signals of the sample 5 was greatly different from that of the sample 6. Specifically, in the sample 5, the signal intensity sharply rises immediately after the start of the sample gas injection period, and then asymptotically approaches the saturation value while further increasing the signal intensity, whereas in the sample 6, the signal intensity when the signal intensity sharply rises immediately after the start of the sample gas injection period is smaller than that in the sample 5, and an amount of change in the signal intensity when asymptotically approaching the saturation value falls within the range of about 0.1 mV. As a result, a significant differ-ence occurs in the saturation value of the signal intensity between the sample 5 and the sample 6. In addition, regard-ing the behavior (the tendency of decrease in the signal intensity) from the sharp falling of the signal intensity immediately after the switching from the sample gas injec-tion period to the purge period to the convergence (return) to the baseline, the sharp falling of the signal intensity occurs in both of the sample 5 and the sample 6, but in the sample 5, the signal intensity slowly converges from a higher signal intensity value to the baseline than in the sample 6, and in the sample 6, the signal intensity converges in a shorter time and returns to the baseline.

In addition, the same measurement results as in a case of using the sensitive film material of ChA shown in FIG. 6 were also obtained in a case of using the sensitive film materials of ChB, ChD, and ChE shown in FIGS. 7 to 9.

From these results, it was found that by MSS using sensitive film materials of ChA, ChB, ChD, and ChE, it was possible to determine ketosis from the measurement results of each alone. More specifically, it was found that a differ-ence between the milk determined to be negative and the milk determined to be strongly positive by the semi-quan-titative method using the test paper described above can be clearly distinguished by applying an appropriate offset treat-ment to the measurement result. In addition, it was sug-gested that the determination accuracy of ketosis can be further enhanced by combining a plurality of measurement results obtained using these MSS.

Furthermore, although not shown, in the MSS using the sensitive film material of ChC, similarly to the MSS using the sensitive film materials of ChA, ChB, ChD, and ChE, a result indicating that it is possible to determine the ketosis from the single measurement result was obtained, but it was suggested that it is more preferable to combine a plurality of measurement results. In other words, it was suggested that the MSS using the sensitive film material of ChC is more suitable for determination by combination with the MSS using the sensitive film materials of ChA, ChB, ChD, and ChE (or other gas detection means including a surface stress sensor of a type different from the MSS).

<Test 4: Measurement (2) of Gas Generated from Milk of a Cow Suffering from Ketosis>

10 mL of milk determined to be false positive to positive (BHBA concentration: 100 to 200 μM) by a test using a product for semi-quantifying β-hydroxybutyric acid in milk (San Keto Paper, SANWA KAGAKU KENKYUSYO Co., Ltd.) (the sample 7) and 10 mL of milk determined to be negative (BHBA concentration: 0 to 50 μM) (the sample 8) were each contained in a vial, and the following two kinds of measurement under different temperature conditions were performed.

In addition, measurement of the sample 7 and the sample 8 was performed using samples refrigerated immediately after breast milk collection.

[Measurement a]

In Measurement a, the vial was placed in an ambient temperature (about 20° C.) environment, and the measure-ment system was an open system. During the measurement, the temperature of the sensor module was stable at about 36.5° C.

Other measurement conditions such as the flow rates of the sample gas and the purge gas other than the temperature conditions of the vial were the same as in Test 1.

[Measurement b]

In Measurement b, the vial was placed in a hot water bath set at about 30° C., and the measurement system was an open system. During the measurement, the temperature of the sensor module was stable at about 36.5° C.

Other measurement conditions such as the flow rates of the sample gas and the purge gas other than the temperature conditions of the vial were the same as in Test 1.

The results of Measurement a and Measurement b are shown in FIGS. 10-11 and FIGS. 12-14, respectively.

Figure 10:
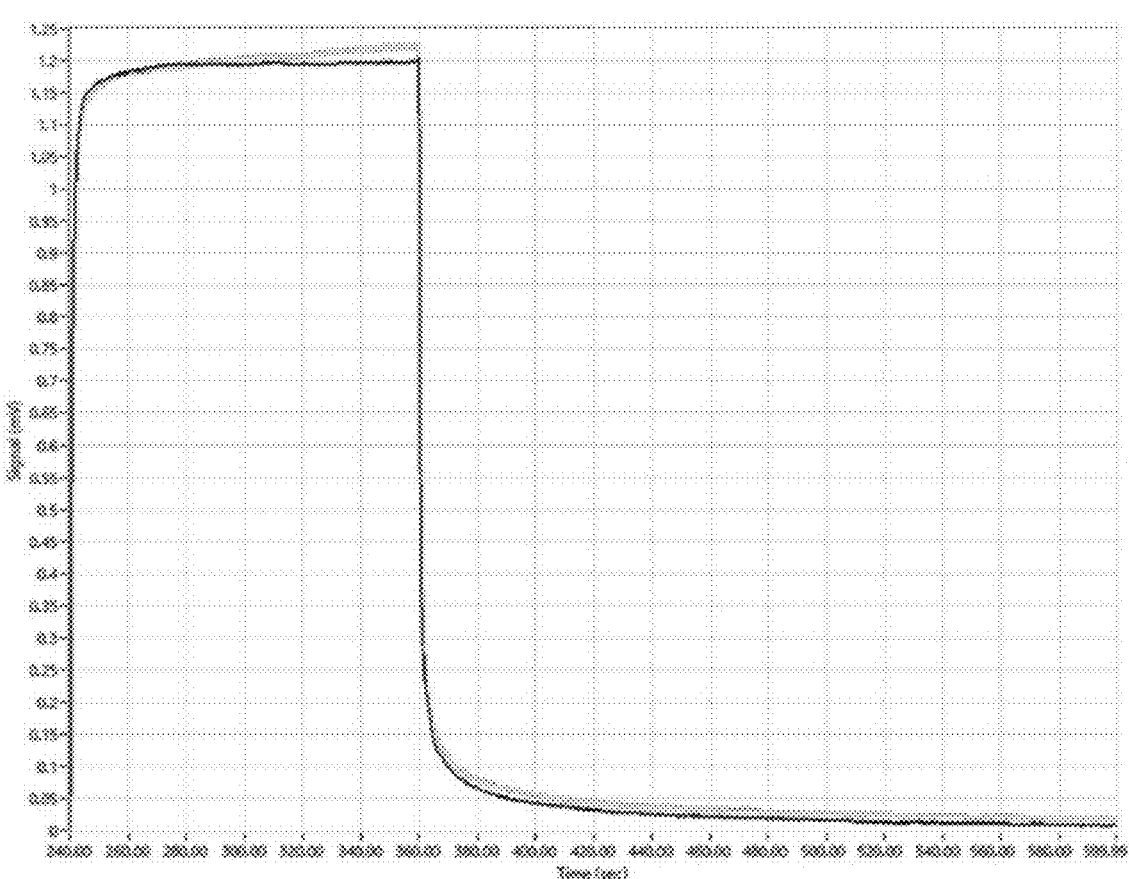
FIG. 10 shows graphs indicating temporal changes (unit: second) of signals (unit: mV) from the MSS of ChA in Measurement a for Test 4 of the examples.

FIG. 10 shows graphs indicating temporal changes (unit: second) of signals (unit: mV) from the MSS of ChA at Measurement a.

Figure 11:
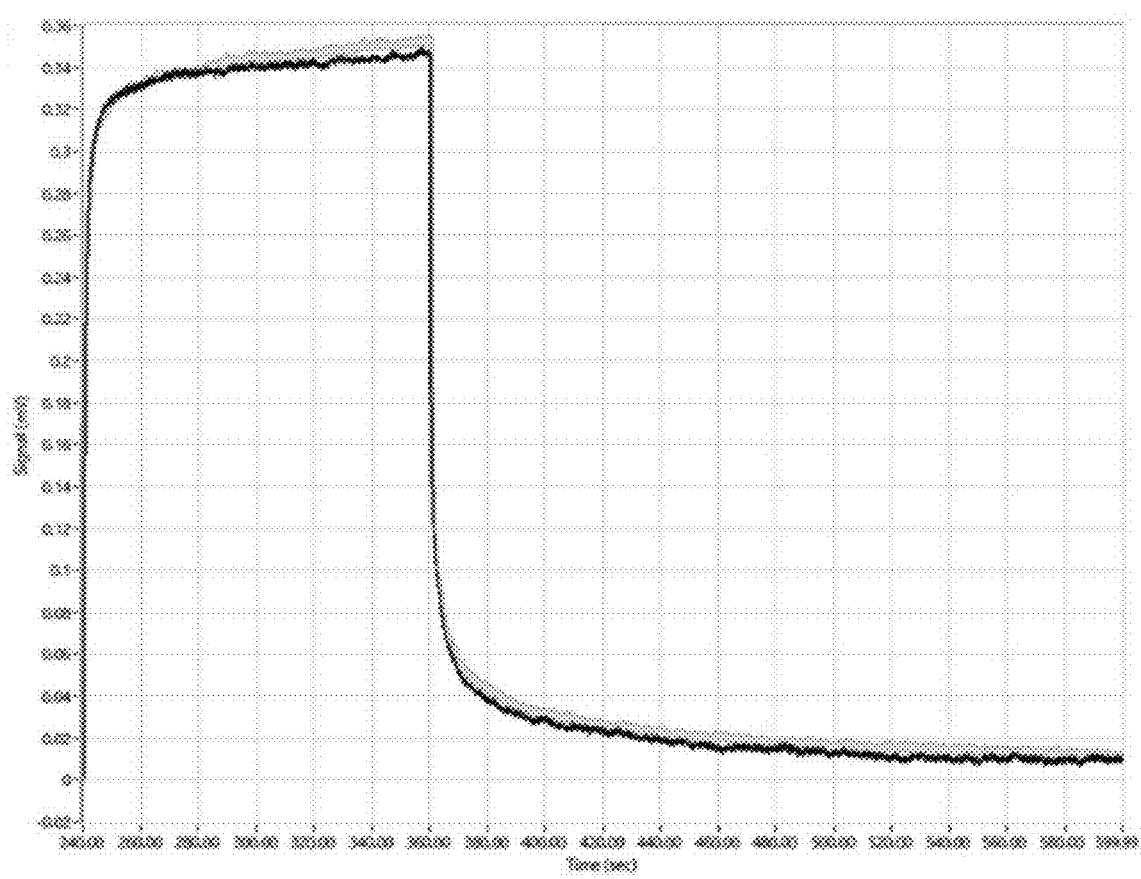
FIG. 11 shows graphs indicating temporal changes (unit: second) of signals (unit: mV) from the MSS of ChD in Measurement a for Test 4 of the examples.

FIG. 11 shows graphs indicating temporal changes (unit: second) of signals (unit: mV) from the MSS of ChD at Measurement a.

Figure 12:
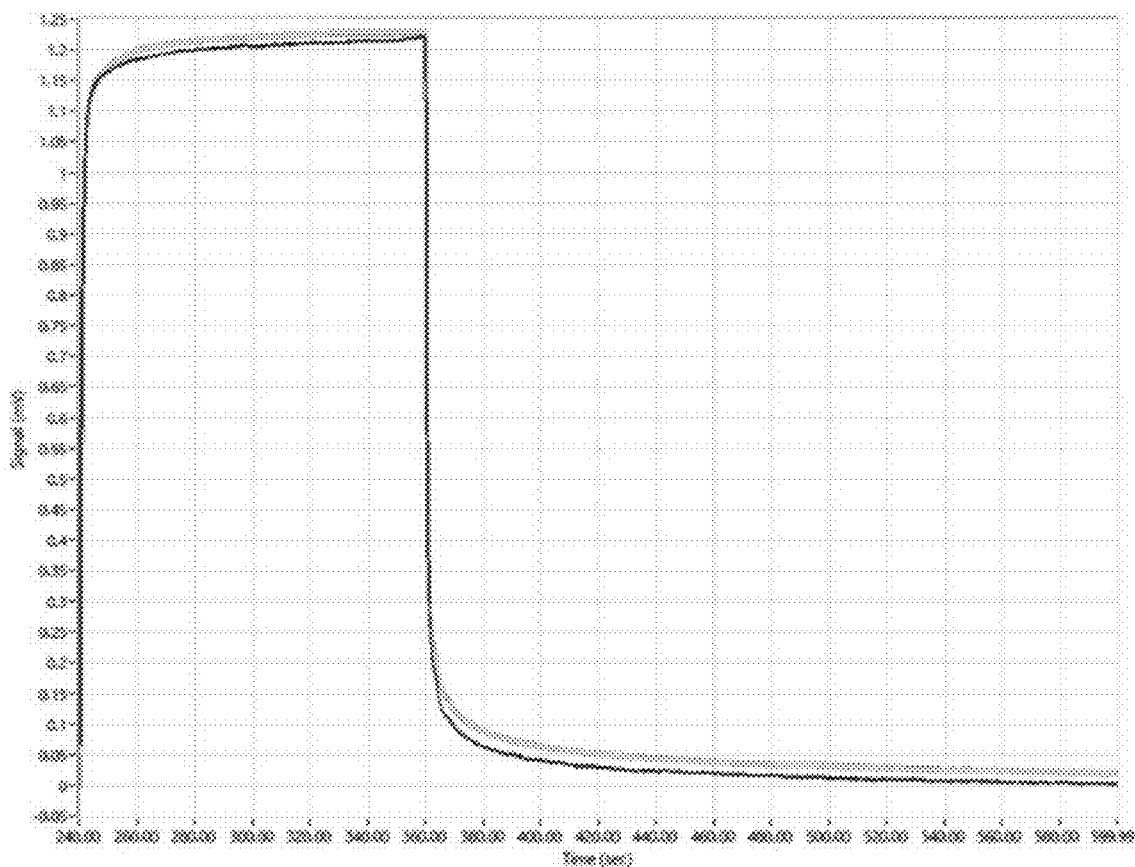
FIG. 12 shows graphs indicating temporal changes (unit: second) of signals (unit: mV) from the MSS of ChA in Measurement b for Test 4 of the examples.

FIG. 12 shows graphs indicating temporal changes (unit: second) of signals (unit: mV) from the MSS of ChA at Measurement b.

Figure 13:
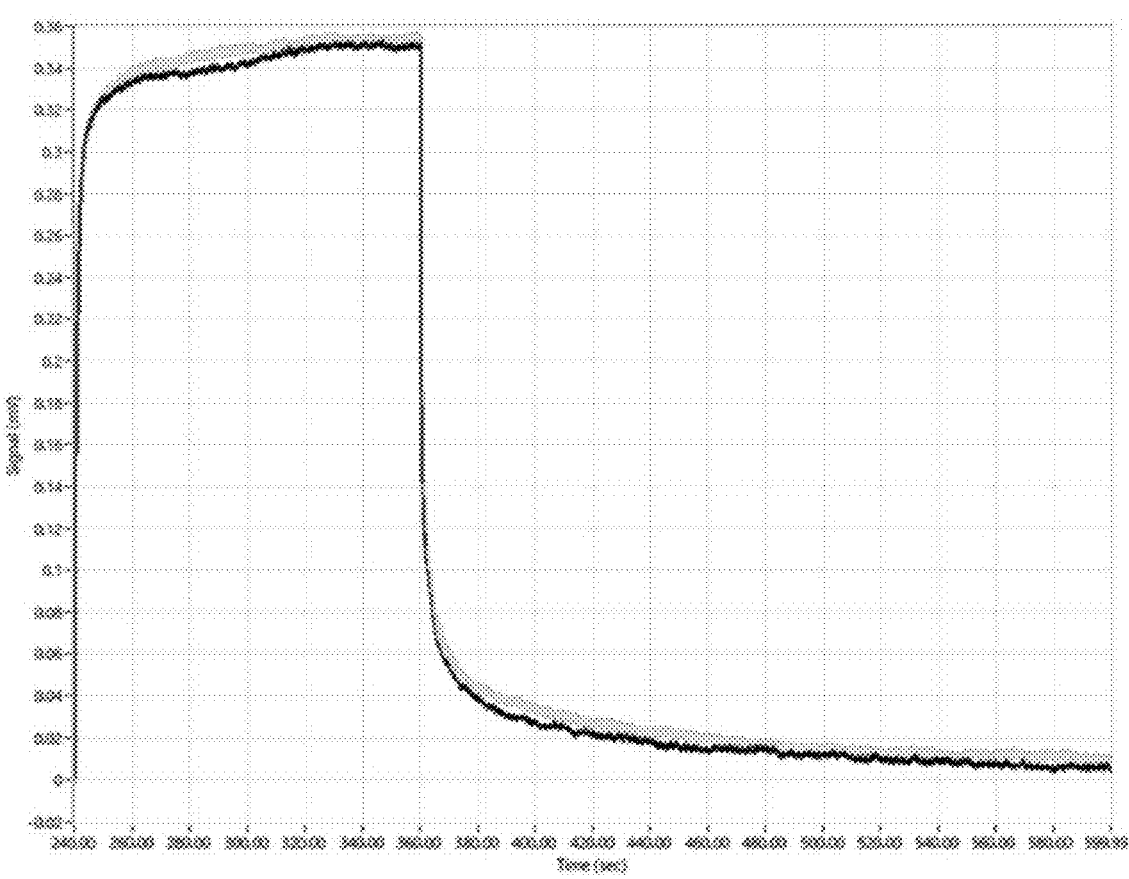
FIG. 13 shows graphs indicating temporal changes (unit: second) of signals (unit: mV) from the MSS of ChD in Measurement b for Test 4 of the examples.

FIG. 13 shows graphs indicating temporal changes (unit: second) of signals (unit: mV) from the MSS of ChD at Measurement b.

Figure 14:
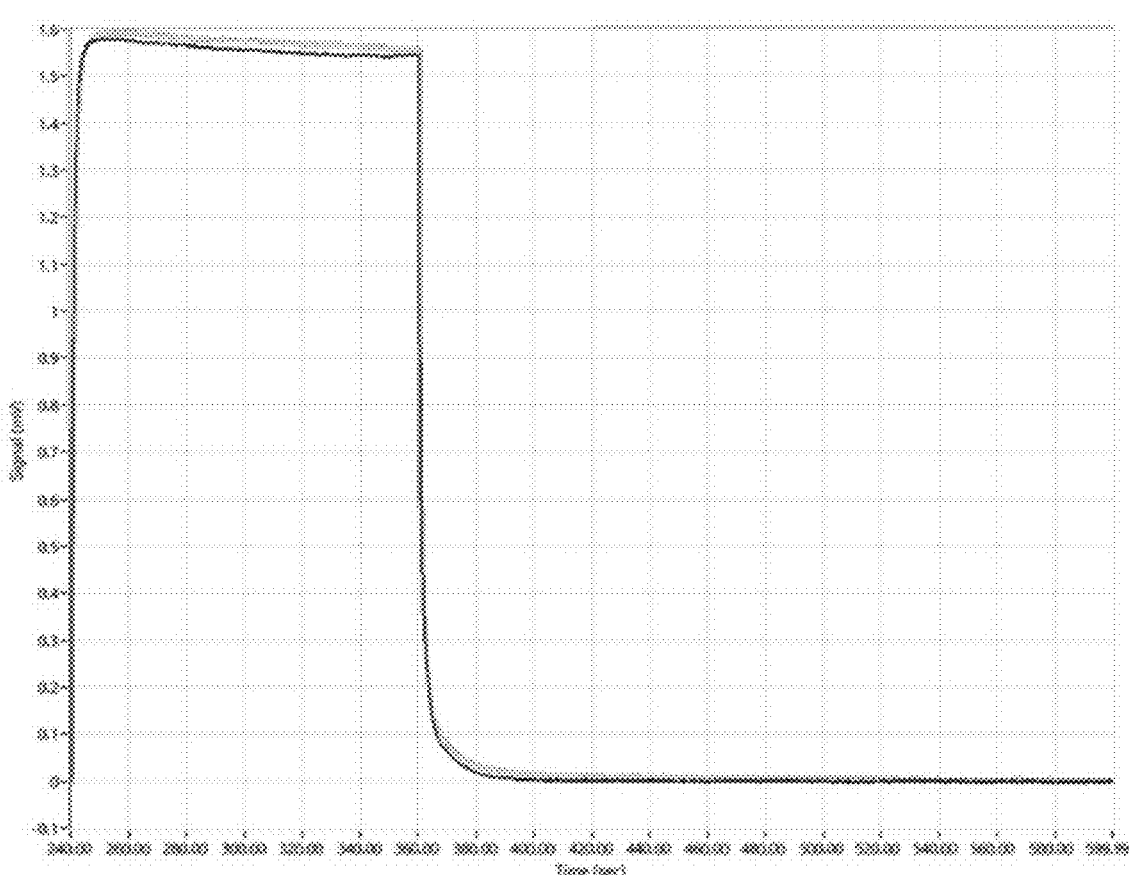
FIG. 14 shows graphs indicating temporal changes (unit: second) of signals (unit: mV) from the MSS of ChE in Measurement b for Test 4 of the examples.

FIG. 14 shows graphs indicating temporal changes (unit: second) of signals (unit: mV) from the MSS of ChE at Measurement b.

In FIGS. 10-14, the measurement result of the sample 7 is shown in light gray, and the measurement result of the sample 8 is shown in dark black.

As can be seen from FIG. 10, in Measurement a, when the sensitive film material of ChA was used, a difference in the temporal changes of the signals was confirmed between the sample 7 and the sample 8. Specifically, the signal intensity sharply rises immediately after the start of the sample gas injection period, and then the behavior of asymptotically approaching the saturation value is different. In addition, there is also a difference in behavior (a tendency of decrease in the signal intensity) from a sharp falling of the signal intensity immediately after switching from the sample gas injection period to the purge period to convergence (return) to the baseline. Furthermore, there is also a difference in the saturation value of the signal intensity.

Here, referring to FIG. 12 showing the result in a case of using the sensitive film material of ChA in Measurement b, it can be seen that the temporal changes of the signals of the sample 7 is greatly different from that of the sample 8 from the result shown in FIG. 10. Specifically, in the sample 8, there was no particular difference between the result obtained in Measurement a and the result obtained in Measurement b, but in the sample 7, in the result obtained in measurement b, the signal intensity value at the time of sharp falling of the signal intensity immediately after switching from the sample gas injection period to the purge period is higher than the result obtained in Measurement a, and the signal intensity value gradually converges from the value toward the baseline. As a result, in the result of Measurement b shown in FIG. 12, the difference in the decreasing behavior of the signal intensity during the purge period between the sample 7 and the sample 8 is clearer.

From these results, it was suggested that by appropriately controlling the temperature of the vial containing the sample in addition to selecting an appropriate material as the sensitive film material of the MSS, the measurement accuracy of the gas generated from the sample (milk) can be further improved, and furthermore, the presence or absence of the determination accuracy of ketosis and/or the possibility of ketosis can be further improved.

In addition, the measurement results having the same characteristics as those in the case of using the sensitive film material of ChA shown in FIGS. 10 and 12 were also obtained in the case of using the sensitive film material of ChD shown in FIGS. 11 and 13.

In addition, although not shown, also in a case of using the sensitive film material of ChB, the measurement results having the same characteristics as those in a case of using the sensitive film materials of ChA and ChD were obtained, but the correlation between the difference in the temperature conditions of the vial and the measurement results was more remarkable in the case of using the sensitive film materials of ChA and ChD.

Furthermore, in a case of using the sensitive film material of ChE, the difference in the temporal changes of the signals between the sample 7 and the sample 8 was not clear in Measurement a, whereas in Measurement b, as shown in FIG. 14, the temporal changes of the signals of the sample 7 was different from that of the sample 8 as comparable to the case of using the sensitive film materials of ChA and ChD (FIGS. 12 and 13).

From these results, it was found that, in the measurement by MSS using the sensitive film materials of ChA and ChD, by maintaining the temperature of the vial containing the sample at an arbitrary value, it is possible to determine at a stage where there is a possibility of ketosis from the measurement results of each alone. More specifically, it was found that the difference between the milk determined to be false positive to positive and the milk determined to be negative by the semi-quantitative method using the test paper described above can be clearly distinguished by applying an appropriate offset treatment to the measurement result. Furthermore, it was found that the determination accuracy can be further improved by setting the temperature of the vial to an appropriate value. These findings are similarly applied to the MSS using the sensitive film material of ChB. Furthermore, it was suggested that depending on the combination of the temperature of the vial containing the sample and the sensitive film material of the MSS, it may be possible to determine the ketosis from a measurement result alone, or a measurement result useful for determination by a combination with the MSS using another sensitive film material (or another gas detection means including a surface stress sensor of a type different from the MSS) may be obtained.

<Test 5: Measurement of Gas Generated from Urine of a Cow Suffering from Ketosis>

[Proton Transfer Reaction Time-of-Flight Mass Spectrometry Using Milk and Urine]

In the measurement of the sample using the measurement system, milk and urine collected from the cow suffering from ketosis and the healthy cow were measured by the proton transfer reaction time-of-flight mass spectrometry (PTR-TOF-MS).

Figure 15A:
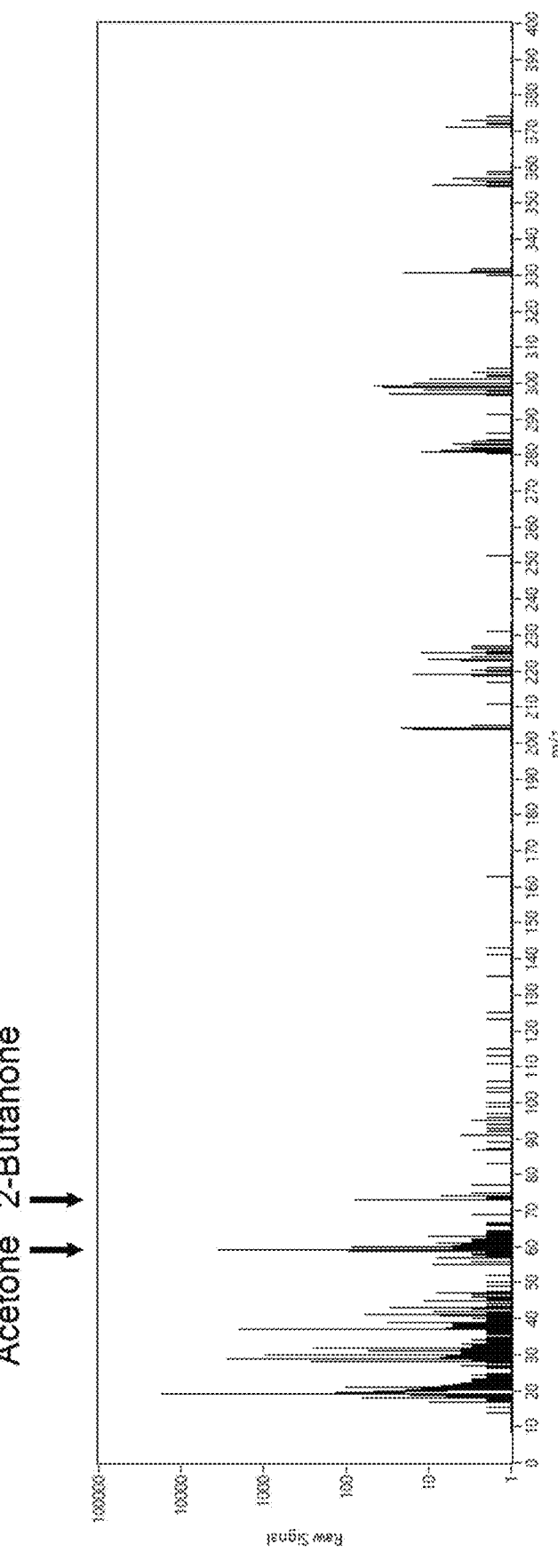
FIG. 15A shows a mass spectrum obtained by proton transfer reaction time-of-flight mass spectrometry (PTR-TOF-MS) of milk of a cow suffering from ketosis in Test 5 of the examples.
Figure 15B:
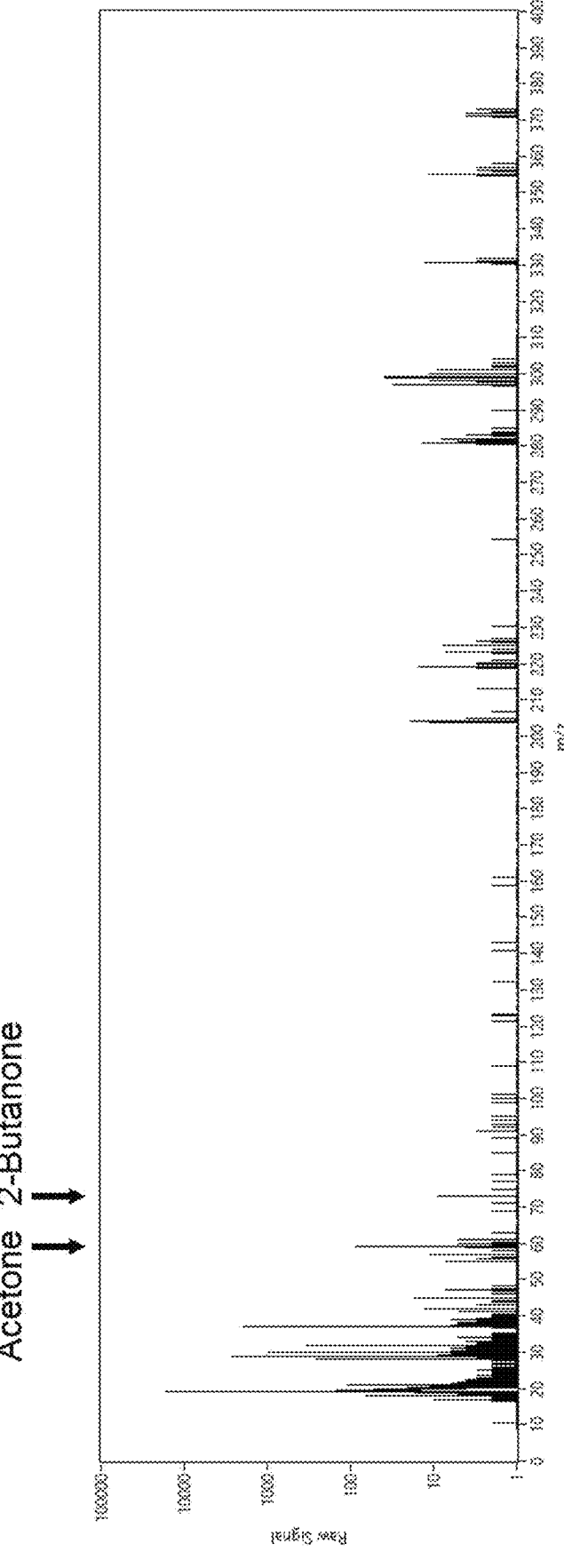
FIG. 15B shows a mass spectrum obtained by PTR-TOF-MS of milk of a healthy cow in Test 5 of the examples.

FIGS. 15A and 15B show the mass spectra obtained by PTR-TOF-MS of milk of a cow suffering from ketosis and milk of a healthy cow, respectively.

Here, the cow suffering from ketosis is a dairy cow determined to be positive to strongly positive (BHBA concentration: 200 to 1000 $\mu$M) by a test using a product that semi-quantifies $\beta$-hydroxybutyric acid in milk (San Keto Paper, SANWA KAGAKU KENKYUSYO Co., Ltd.), and a healthy cow is a dairy cow determined to be negative (BHBA concentration: 0 to 50 $\mu$M) by the above test. Amount of the milk sample used for the measurement was 2 mL, and a dilution ratio of the gas was 100 times. The same applies to the measurement of urine samples (FIGS. 16A and 16B) to be described later.

As can be seen from FIGS. 15A and 151B, in the mass spectra of the milk of the cow suffering from ketosis and the milk of the healthy cow, peak positions (m/z values) were highly similar, but the peak intensities with the m/z values in the range of about 50 to 80 were significantly different between the cow suffering from ketosis and the healthy cow, and as a result of analysis, it was confirmed that peaks derived from acetone and 2-butanone were included as shown by arrows in each figure.

Figure 16A:
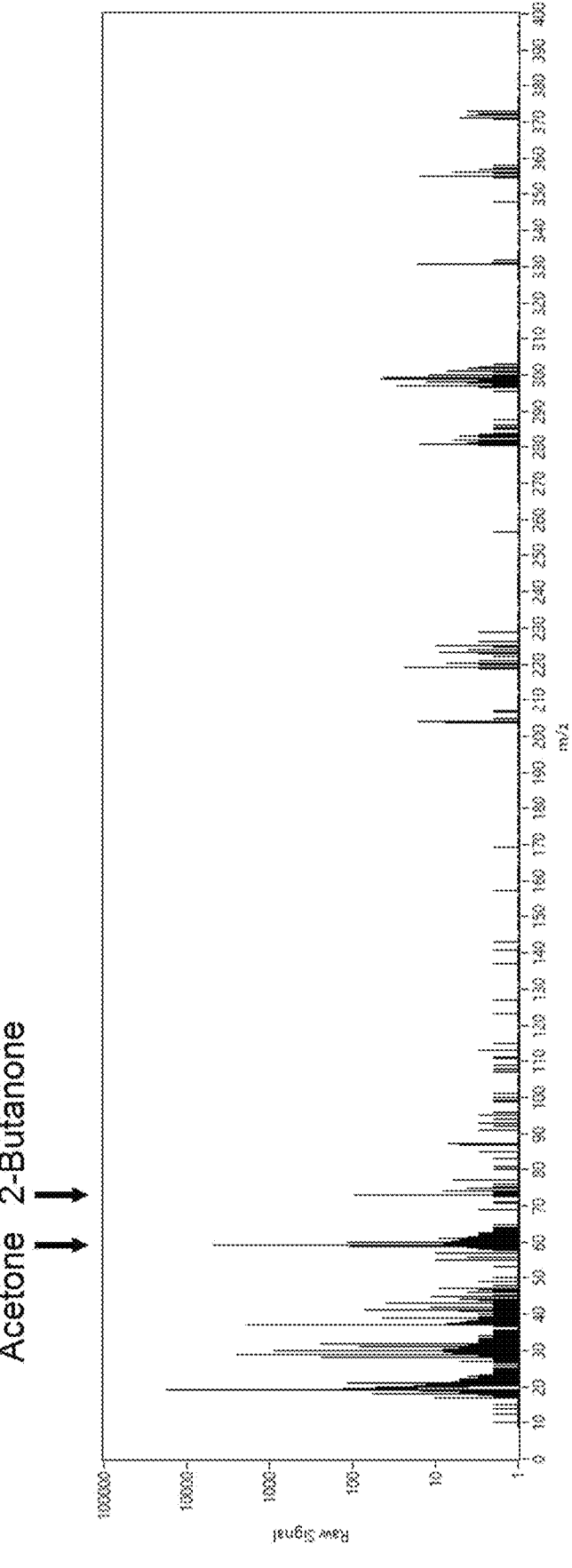
FIG. 16A shows a mass spectrum obtained by PTR-TOF-MS of urine of a cow suffering from ketosis in Test 5 of the examples.
Figure 16B:
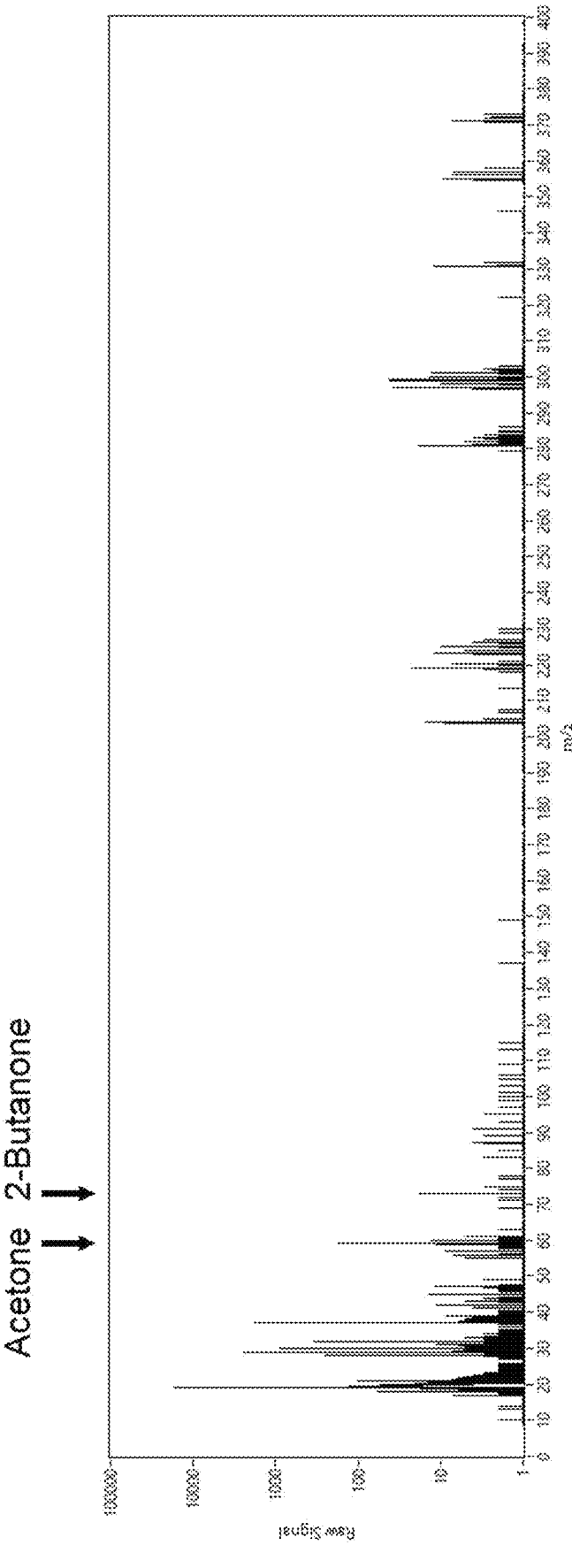
FIG. 16B shows a mass spectrum obtained by PTR-TOF-MS of urine of a healthy cow in Test 5 of the examples.

FIGS. 16A and 16B show the mass spectra obtained from PTR-TOF-MS of urine of the cow suffering from ketosis and urine of the healthy cow, respectively.

Also in the mass spectra of FIGS. 16A and 16B, the same results as those of the milk sample described above were obtained. In other words, in the mass spectra of urine from the cow suffering from ketosis and urine from the healthy cow, the peak positions (the m/z values) were highly similar, but peak intensities with the m/z values in the range of about 50 to 80 were significantly different between the cow suffering from ketosis and the healthy cow, and as a result of analysis, it was confirmed that the peaks derived from acetone and 2-butanone were included as indicated by arrows in each figure.

Furthermore, interestingly, comparing FIG. 15A with FIG. 16A and FIG. 15B with FIG. 16B, it is found that the mass spectra of milk and urine of the cow suffering from ketosis and the mass spectra of milk and urine of the healthy cow have almost the same overall peak profiles. Therefore, the concentrations of acetone and 2-butanone, which are characteristic components in these samples, were further analyzed.

Figure 17A:
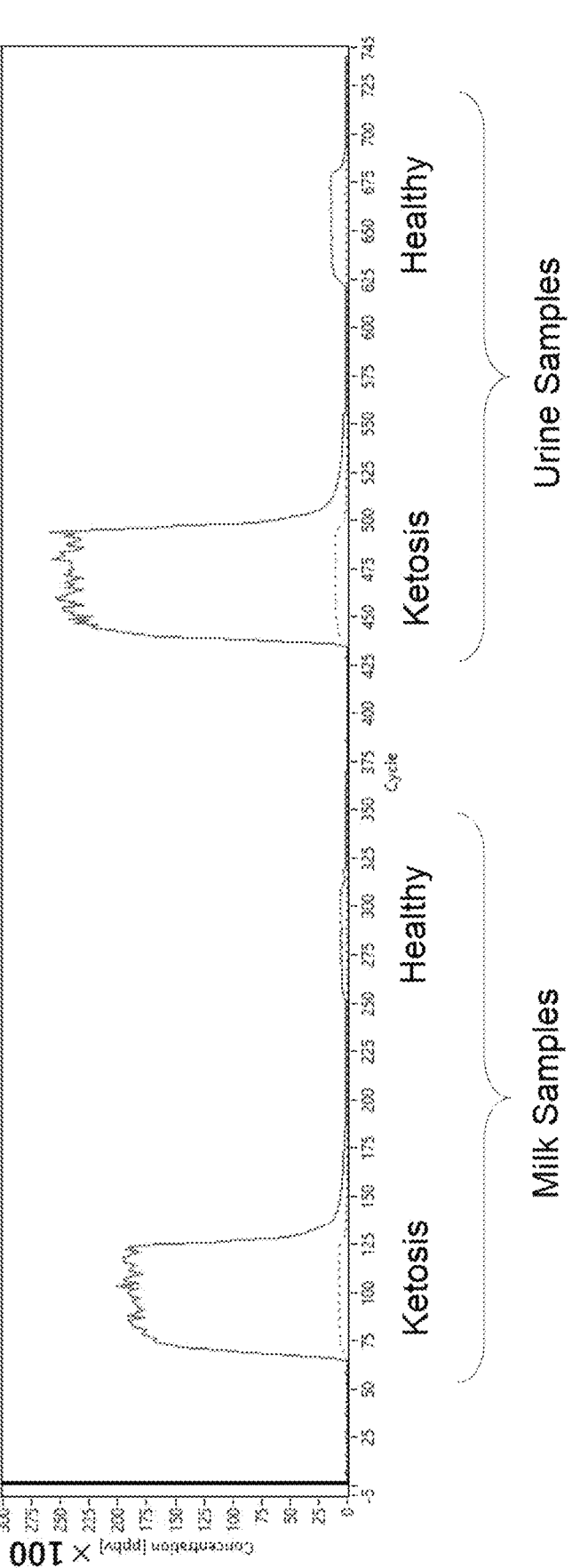
FIG. 17A shows measurement results of concentrations of acetone and 2-butanone by PTR-TOF-MS in the milk and urine of a cow suffering from ketosis and the milk and urine of a healthy cow in Test 5 of the examples.
Figure 17B:
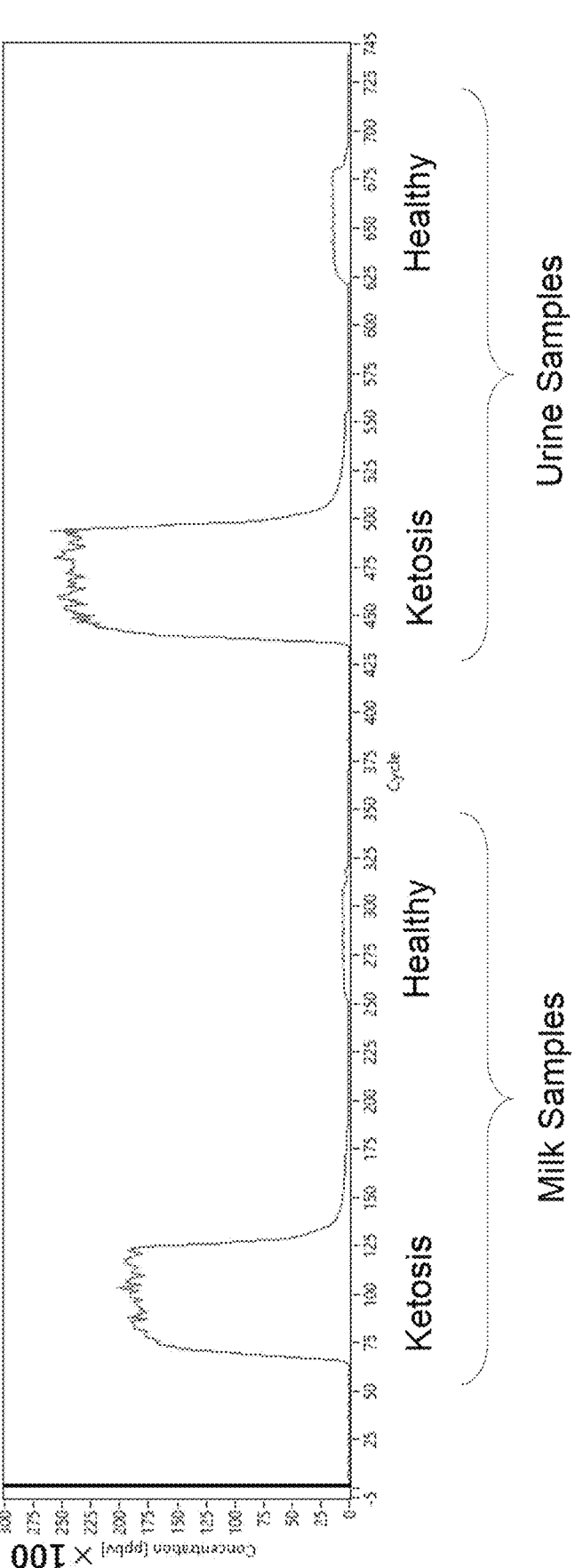
FIG. 17B shows the measurement result of concentration of acetone among the measurement results shown in FIG. 17A.
Figure 17C:
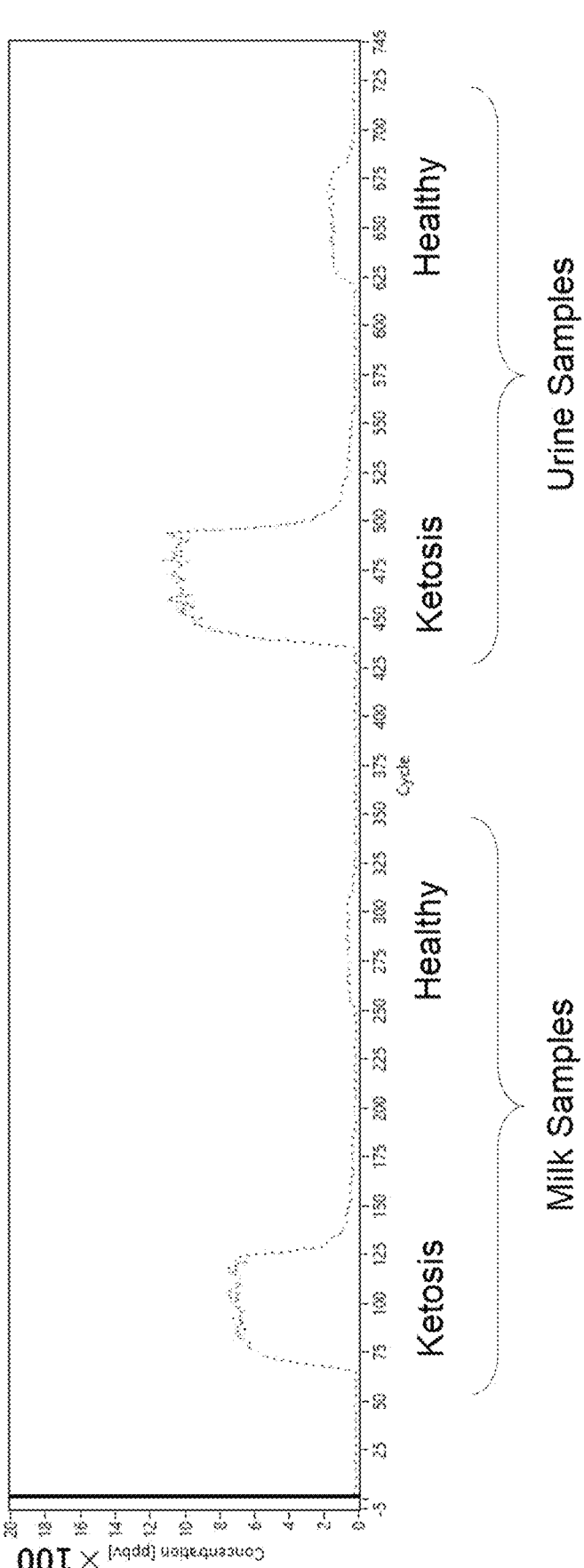
FIG. 17C shows the measurement results of concentration of 2-butanone among the measurement results shown in FIG. 17A.

FIGS. 17A, 17B, and 17C show the measurement results of the concentrations of acetone and 2-butanone by PTR-TOF-MS in the milk and urine of the cow suffering from ketosis and the milk and urine of the healthy cow. FIG. 17A shows the measurement results of the concentrations of acetone and 2-butanone together, where a solid line refers to acetone and a broken line refers to 2-butanone. FIGS. 17B and 17C separately show the measurement results of the concentrations of acetone and 2-butanone shown in FIG. 17A, FIG. 17B shows acetone, and FIG. 17C shows 2-butanone.

From the measurement results shown in FIGS. 17A-17C, it was found that in the present test, the concentrations of acetone and 2-butanone, which are characteristic components in the milk and urine collected from the cow suffering from ketosis and the healthy cow, are very close in values between the milk and urine of the cow suffering from ketosis and the milk and urine of the healthy cow. Furthermore, it was found that the difference was small, and it can be considered that they are almost the same.

As described above, the results of PTR-TOF-MS shown in FIGS. 15A and 15B, FIGS. 16A and 16B, and FIGS. 17A-17C indicate that the correlation between the presence or absence of ketosis and the content (concentration) of a specific component (for example, acetone and 2-butanone) in the composition of the gas generated from the body fluid is common even in different kinds of body fluids such as milk and urine of dairy cows, and suggest that it is possible to determine the ketosis by using the gas generated from not only the milk used for the measurement in Tests 1 to 4 but also body fluids other than the milk collected from animals, for example, blood, urine, saliva, and sweat.

[Measurement of Urine Sample]

Next, based on the findings mentioned above, 2 mL of urine from the cow suffering from ketosis (the sample 9) and 2 mL of urine from the healthy cow (the sample 10) were each contained in a vial and measured.

In the measurement of the sample 9 and the sample 10, the vial was placed in an ambient temperature (about 25° C.) environment, and the measurement system was an open system. During the measurement, the temperature of the sensor module was stable at about 36.5° C.

Other measurement conditions such as the flow rates of the sample gas and the purge gas were the same as in Test 1.

The results are shown in FIGS. 18-22.

Figure 18:
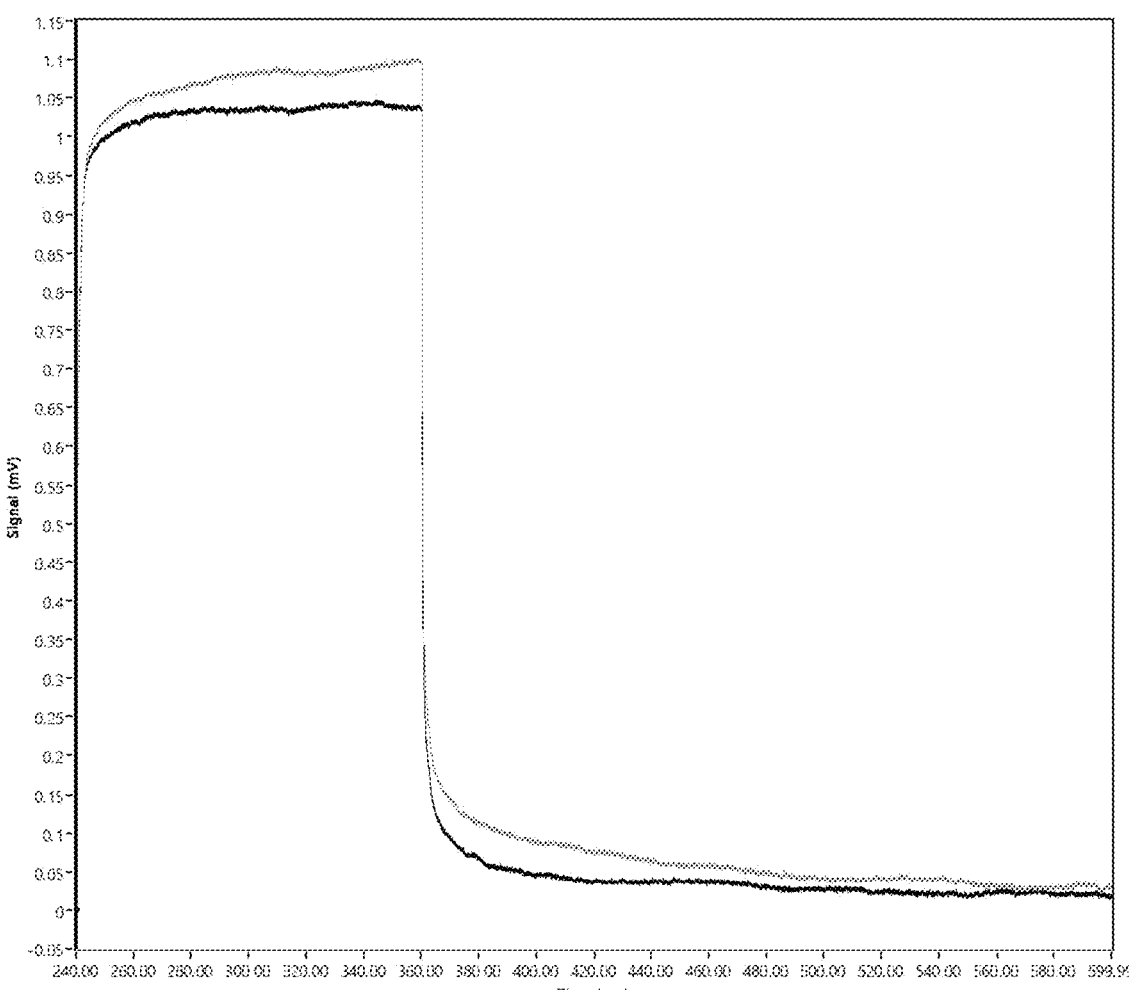
FIG. 18 shows graphs indicating temporal changes (unit: second) of signals (unit: mV) from the MSS of ChA for Test 5 of the examples.

FIG. 18 shows graphs indicating temporal changes (unit: second) of signals (unit: mV) from the MSS of ChA.

Figure 19:
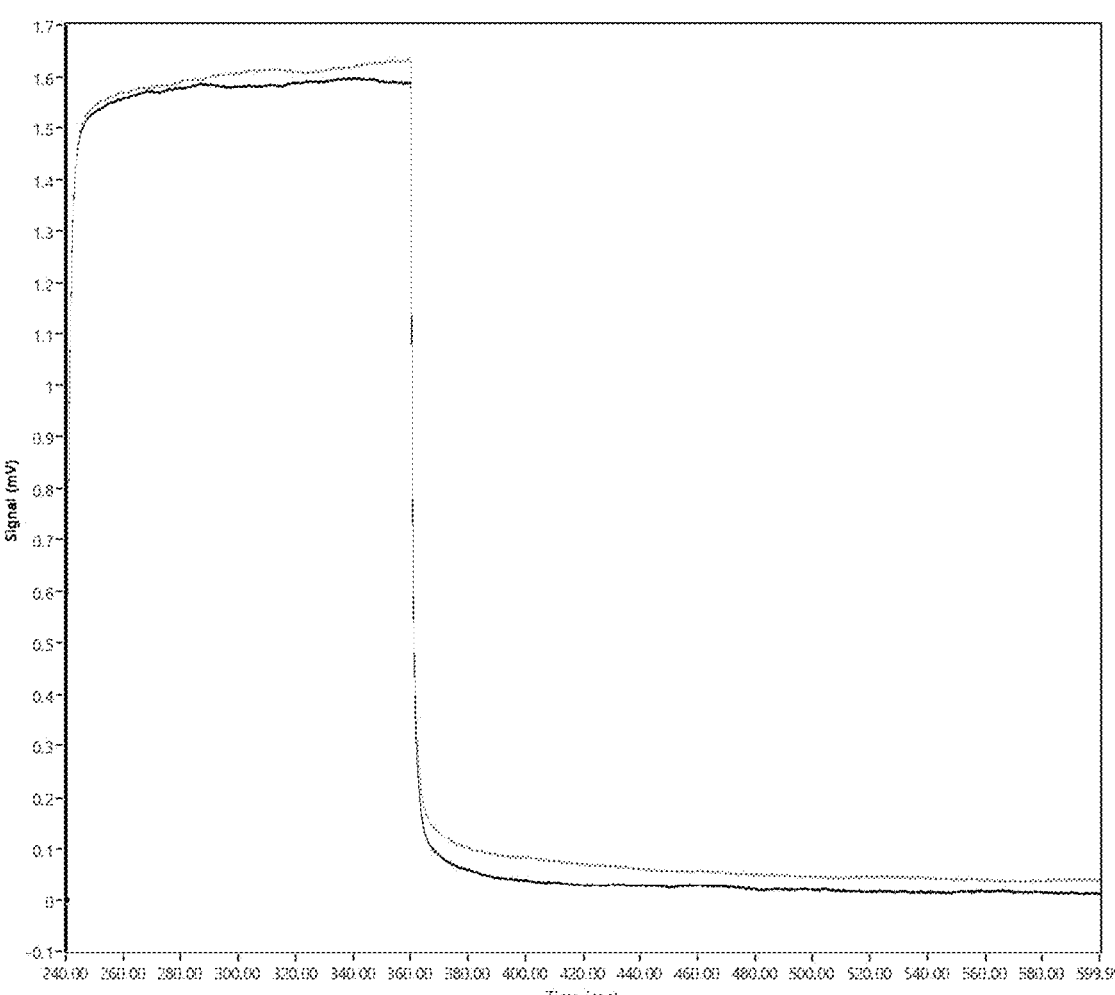
FIG. 19 shows graphs indicating temporal changes (unit: second) of signals (unit: mV) from the MSS of ChB for Test 5 of the examples.

FIG. 19 shows graphs indicating temporal changes (unit: second) of signals (unit: mV) from the MSS of ChB.

Figure 20:
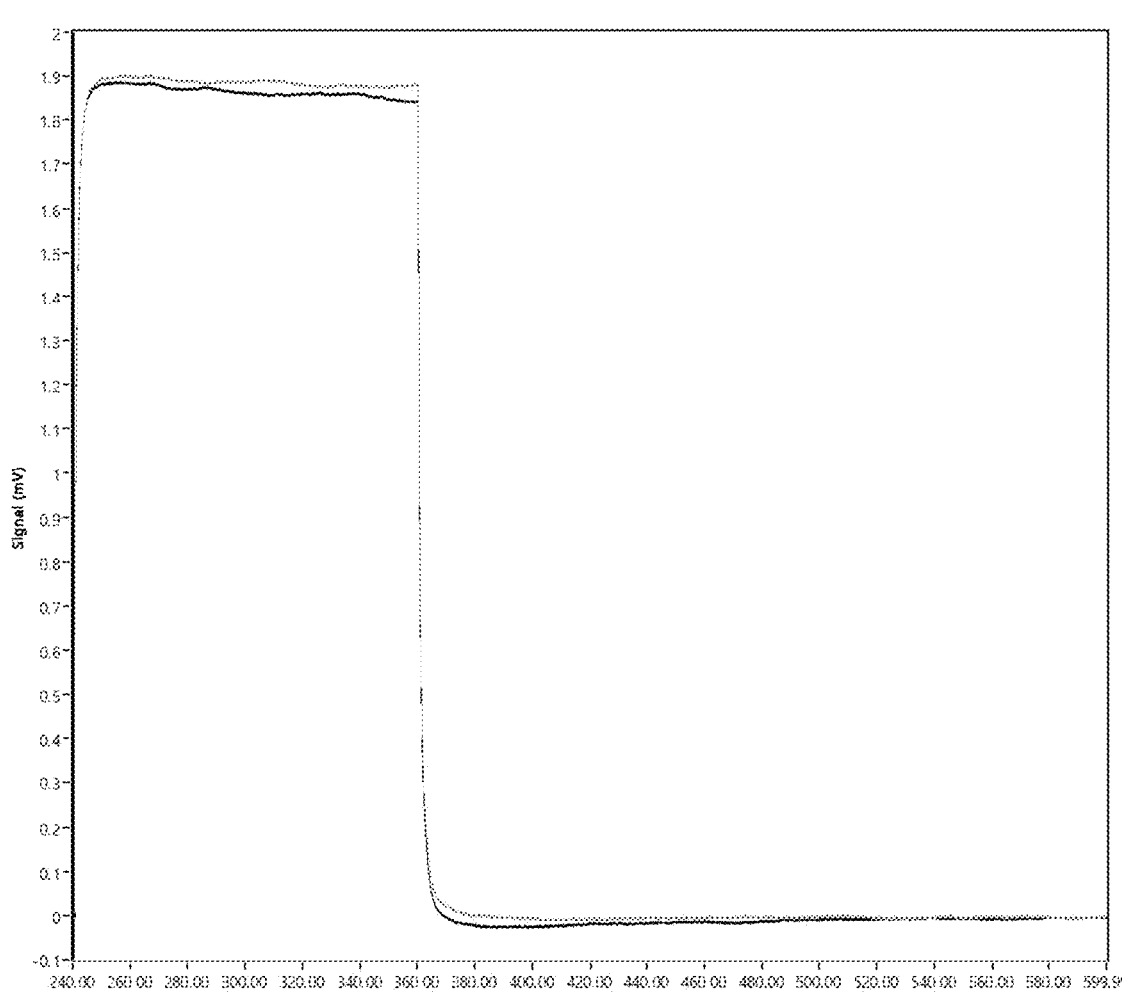
FIG. 20 shows graphs indicating temporal changes (unit: second) of signals (unit: mV) from an MSS of ChC in Test 5 of the examples.

FIG. 20 shows graphs indicating temporal changes (unit: second) of signals (unit: mV) from the MSS of ChC.

Figure 21:
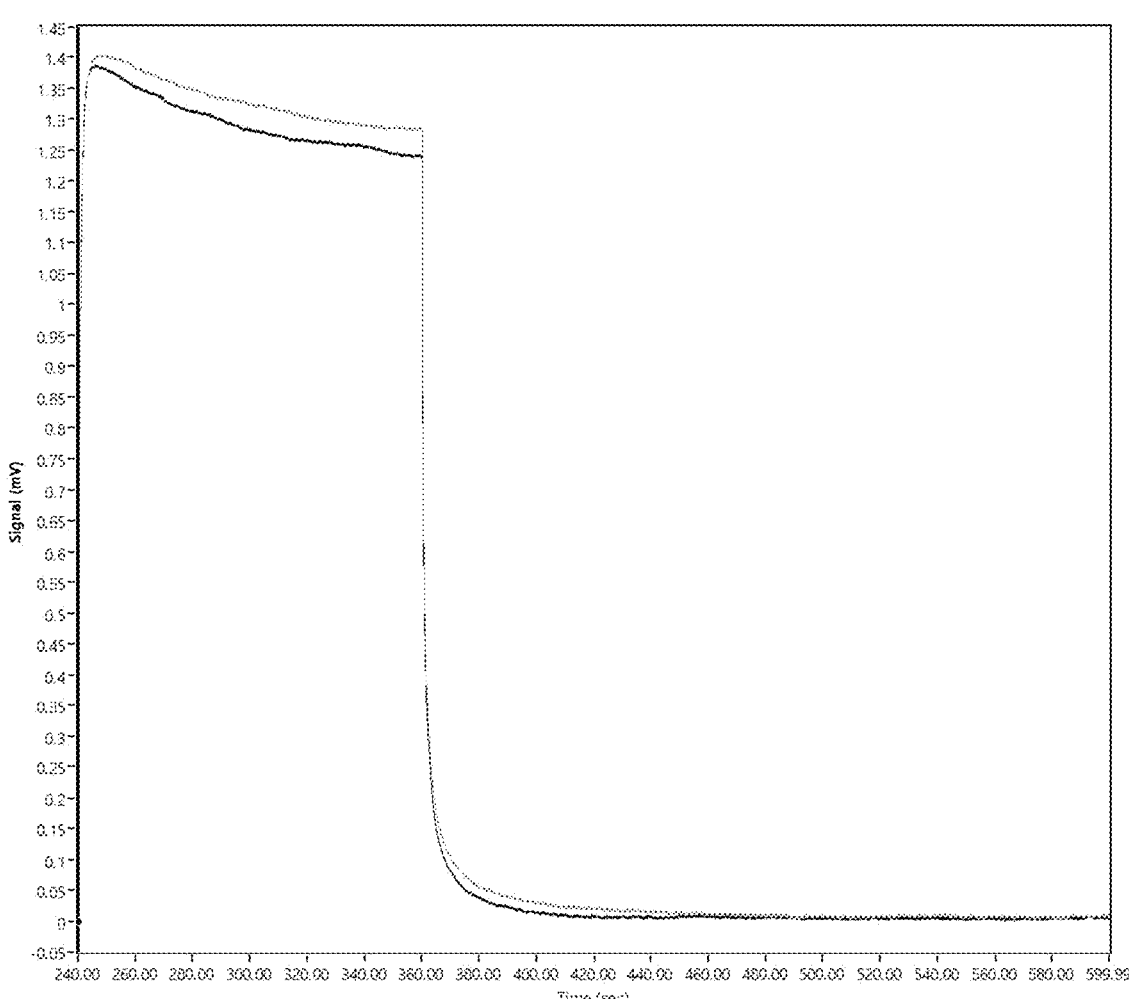
FIG. 21 shows graphs indicating temporal changes (unit: second) of signals (unit: mV) from an MSS of ChF for Test 5 of the examples.

FIG. 21 shows graphs indicating temporal changes (unit: second) of signals (unit: mV) from the MSS of ChF.

Figure 22:
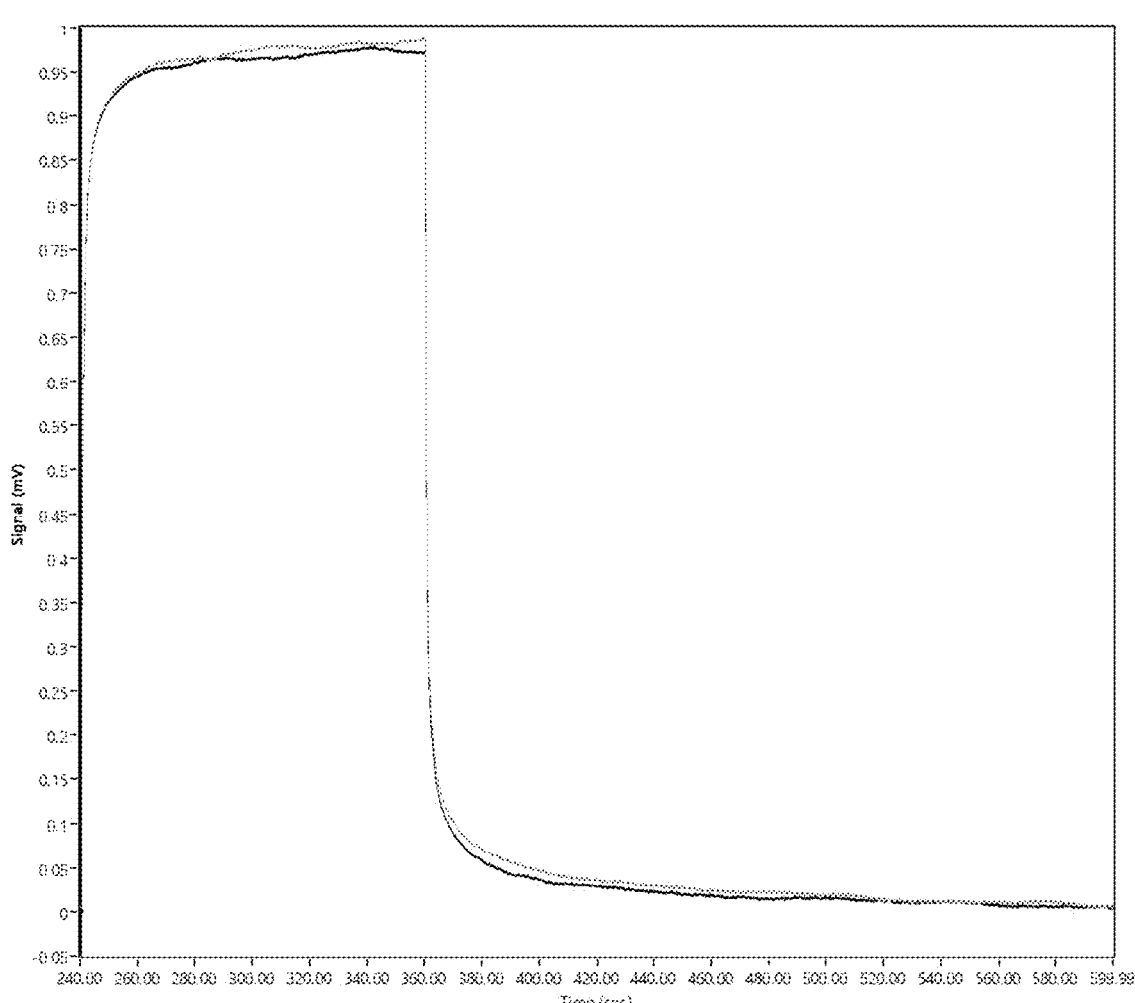
FIG. 22 shows graphs indicating temporal changes (unit: second) of signals (unit: mV) from an MSS of ChG in Test 5 of the examples.

FIG. 22 shows graphs indicating temporal changes (unit: second) of signals (unit: mV) from the MSS of ChG.

In FIGS. 18-22, the measurement result of the sample 9 is shown in light gray, and the measurement result of the sample 10 is shown in dark black.

As can be seen from FIG. 18, when the sensitive film material of ChA was used, a difference in the temporal changes of the signals was confirmed between the sample 9 and the sample 10. Specifically, the signal intensity sharply rises immediately after the start of the sample gas injection period, and then the behavior of asymptotically approaching the saturation value is different. In addition, there is also a difference in behavior (a tendency of decrease in the signal intensity) from a sharp falling of the signal intensity immediately after switching from the sample gas injection period to the purge period to convergence (return) to the baseline. Furthermore, there is also a difference in the saturation value of the signal intensity.

In addition, the same measurement results as in the case of using the sensitive film material of ChA shown in FIG. 18 were also obtained in the case of using the sensitive film materials of ChB, ChC, ChF, and ChG shown in FIGS. 19-22.

From these results, it was found that by MSS using sensitive film materials of ChA, ChB, ChC, ChF, and ChG, it is possible to determine the ketosis from the measurement results of each of them alone. More specifically, it was found that by applying an appropriate offset treatment to the measurement result, it is possible to clearly distinguish the difference between the urine of the dairy cow determined to be negative and the urine of the dairy cow determined to be positive to strong positive by the semi-quantitative method using the test paper described above. In addition, it was suggested that the determination accuracy of ketosis can be further enhanced by combining a plurality of measurement results obtained using these MSS.

For example, as the measurement system in a case where both milk and urine can be acquired relatively easily (so as not to impose an additional burden on animals) as the sample to be examined, an MSS using the sensitive film material of ChA is used alone, a gas generated from milk and a gas generated from urine are measured, and the ketosis can be determined based on the result.

In addition, as an example of the case of using a plurality of sensitive film materials, the measurement system including an aggregate of MSS to which the sensitive film materials of ChA to ChG are applied is configured, and in the MSS using the sensitive film materials of ChA, ChB, and ChC, a gas generated from milk and a gas generated from urine are measured, in the MSS using the sensitive film materials of ChD and ChE, a gas generated from milk is measured, and in the MSS using the sensitive film materials of ChF and ChG, a gas generated from urine is measured, and by combining these results, it is also possible to determine the ketosis.

INDUSTRIAL APPLICABILITY

When milk is used as a body fluid to be examined, the present invention is typically suitable for application to dairy cows. In addition, the present invention is suitably applied to animals bred for producing milk as an industry in addition to dairy cows, for example, animals of bovine family such as goats, sheep, buffalo, and yaks, horses, and the like. More specifically, the present invention is particularly suitable for preliminarily extracting (screening) an individual suffering from ketosis and/or an individual suspected of suffering from ketosis in an animal bred in large numbers to produce milk such as the dairy cows. In addition, the body fluids other than the milk also have different ease of collection depending on the kind of the body fluid, the kind of the animal, and the collection method, and different certainty as to whether or not the body fluid can be obtained at a necessary time point. However, a body fluid that can be appropriately used according to the situation can be used as the target to be examined.

In recent years, in the feeding management systems for dairy cows and the like, efforts have been made for early detection of diseases, signs of physical condition change, and the like by utilizing motion sensors and the like. By combining the present invention with such feeding management system, it is possible to more easily and efficiently perform health management of animals, and it is expected to contribute to improvement or maintenance of productivity.

The invention claimed is:

1. A method for determining ketosis, comprising:

providing gas detection means with a gas generated from a body fluid collected from an animal other than humans; and determining ketosis of the animal based on a composition of the gas generated from the body fluid using a response of the gas detection means to the gas generated from the body fluid, wherein the gas detection means is a gas sensor, the gas sensor being a surface stress sensor, the response of the gas detection means is a signal output from the surface stress sensor, and the determining of ketosis is performed based on a pattern of a temporal change in the signal output from the surface stress sensor, wherein the gas generated from the body fluid and a purge gas are alternately supplied to the surface stress sensor, and the determining of ketosis is performed using the signal output from the surface stress sensor corresponding to the gas generated from the body fluid and the signal output from the surface stress sensor corresponding to the purge gas, wherein an offset treatment is performed to the signal output from the surface stress sensor, a reference point of the offset treatment is set at an end point of a time frame during which the purge gas is given to the surface stress sensor, and a determination point is set at an arbitrary time point when a certain time has elapsed from an end of a time frame during which the gas generated from the body fluid is supplied to the surface stress sensor, and wherein the body fluid is selected from the group consisting of milk, blood, urine, saliva, and sweat.

2. The method for determining ketosis according to claim 1, wherein the gas generated from the body fluid is at least one of ketones, alcohols, aldehydes, nitriles, organic acids, water vapor, nitrogen, oxygen, and carbon dioxide.

3. The method for determining ketosis according to claim 2, wherein the gas generated from the body fluid is at least one of ketones and alcohols, the ketones being acetone, and the alcohols being at least one selected from the group consisting of methanol, ethanol, propanol, and butanol.

4. The method for determining ketosis according to claim 1, wherein, as the gas generated from the body fluid, a gas obtained by passing a gas substantially not containing a component that affects the determination of ketosis through a container containing the body fluid is supplied to the surface stress sensor.

5. The method for determining ketosis according to claim 1, wherein the surface stress sensor is a membrane type surface stress sensor.

6. The method for determining ketosis according to claim 1, wherein at least one selected from the group consisting of poly(4-methylstyrene), poly(2,6-diphenyl-p-phenylene oxide), poly(vinylidene fluoride), cellulose acetate butyrate, poly(ethyleneimine), phenyl group-modified silica/titania composite nanoparticles, and polystyrene is used as a material of a sensitive film of the surface stress sensor.

7. The method for determining ketosis according to claim 6, wherein, as the surface stress sensor, at least a first surface stress sensor using one material selected from the group as the sensitive film and a second surface stress sensor using another material selected from the group as the sensitive film are used.

8. The method for determining ketosis according to claim 1, wherein a time frame during which a predetermined reference gas is given to the surface stress sensor is provided in addition to the time frame during which the gas generated from the body fluid is supplied to the surface stress sensor and the time frame during which the purge gas is given to the surface stress sensor, and the signal output from the surface stress sensor corresponding to the reference gas is further used in the determination of the ketosis.

9. The method for determining ketosis according to claim 8, wherein the predetermined reference gas is a gas generated from a reference body fluid.

10. The method for determining ketosis according to claim 1, wherein a reference gas and the purge gas are alternately supplied to the surface stress sensor to prepare digital data corresponding to the reference gas, the digital data corresponding to the reference gas being based on the signal output from the surface stress sensor corresponding to the reference gas and the signal output from the surface stress sensor corresponding to the purge gas, the gas generated from the body fluid and the purge gas are alternately supplied to the surface stress sensor to prepare digital data corresponding to the body fluid to be measured, the digital data corresponding to the body fluid to be measured being based on the signal output from the surface stress sensor corresponding to the gas generated from the body fluid and the signal output from the surface stress sensor corresponding to the purge gas, and the determination of ketosis is performed based on the digital data corresponding to the reference gas and the digital data corresponding to the body fluid to be measured.

11. The method for determining ketosis according to claim 10, wherein the surface stress sensor to which the reference gas and the purge gas are alternately supplied and the surface stress sensor to which the gas generated from the body fluid and the purge gas are alternately supplied are the same surface stress sensor, or are surface stress sensors that are different from each other.

12. The method for determining ketosis according to claim 1, wherein the gas generated from the body fluid is supplied to an additional gas sensor, and the determination of ketosis is performed based on the signal output from the surface stress sensor and a signal output from the additional gas sensor.

13. An apparatus used for the method for determining ketosis according to claim 1, comprising:

at least one surface stress sensor;

a first gas flow path for supplying a sample gas generated from a body fluid to be examined collected from an animal, the body fluid being selected from the group consisting of milk, blood, urine, saliva, and sweat; and a second gas flow path for supplying a purge gas not containing a gas component to be measured, wherein the sample gas supplied from the first gas flow path and the purge gas supplied from the second gas flow path are alternately switched and supplied to the at least one surface stress sensor to generate a signal from the at least one surface stress sensor, thereby determining ketosis of the animal based on a composition of the gas generated from the body fluid, and wherein the apparatus performs an offset treatment to the signal output from the at least one surface stress sensor, wherein a reference point of the offset treatment is set at an end point of a time frame during which the purge gas is given to the at least one surface stress sensor, and a determination point is set at an arbitrary time point when a certain time has elapsed from an end of a time frame during which the sample gas is supplied to the at least one surface stress sensor.

14. The apparatus according to claim 13, further comprising an additional gas sensor and an additional gas flow path for supplying the sample gas to the additional gas sensor, wherein the determination of ketosis is performed based on the signal output from the at least one surface stress sensor and a signal output from the additional gas sensor.

15. The method for determining ketosis according to claim 1, wherein the presence or absence of ketosis or a possibility of ketosis is determined by obtaining a feature value from the determination point or a value in a vicinity of the determination point, the feature value being at least one selected from the group consisting of a signal intensity after the offset treatment at the determination point, a slope of a graph of the signal output from the surface stress sensor at the determination point, and an average slope or curvature of the graph of the signal output from the surface stress sensor in the vicinity of the determination point.

16. The method for determining ketosis according to claim 1, wherein the presence or absence of ketosis or a possibility of ketosis is determined by observing a signal intensity at a time point of several seconds to tens of seconds after the end of the time frame during which the gas generated from the body fluid is supplied to the surface stress sensor or a change in the signal intensity in the vicinity of the time point.

* * * * *